(12) United States Patent
Shin et al.

(10) Patent No.: US 10,365,800 B2
(45) Date of Patent: Jul. 30, 2019

(54) USER INTERFACE (UI) PROVIDING APPARATUS AND UI PROVIDING METHOD THEREOF

(71) Applicant: SAMSUNG ELECTRONICS CO., LTD., Suwon-si (KR)

(72) Inventors: Dong-yun Shin, Seongnam-si (KR); Hee-won Jung, Suwon-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 240 days.

(21) Appl. No.: 15/105,422

(22) PCT Filed: Dec. 16, 2013

(86) PCT No.: PCT/KR2013/011678
§ 371 (c)(1),
(2) Date: Jun. 16, 2016

(87) PCT Pub. No.: WO2015/093636
PCT Pub. Date: Jun. 25, 2015

(65) Prior Publication Data
US 2016/0320935 A1    Nov. 3, 2016

(51) Int. Cl.
*G06F 3/048* (2013.01)
*G06F 3/0484* (2013.01)
(Continued)

(52) U.S. Cl.
CPC .............. *G06F 3/0484* (2013.01); *G06F 3/14* (2013.01); *G06F 3/167* (2013.01); *G06F 19/00* (2013.01);
(Continued)

(58) Field of Classification Search
CPC .......... G06F 3/011; G06F 3/016; G06F 3/167; G06F 3/30867; H04L 41/22; H04L 67/10; H04M 1/22; H04M 3/42391
See application file for complete search history.

(56) References Cited

U.S. PATENT DOCUMENTS 6,963,937 B1 * 11/2005 Kamper ................. G06F 3/038
                                                            345/156
6,977,579 B2    12/2005 Gilfix et al.
(Continued)

FOREIGN PATENT DOCUMENTS

JP    06-063070 A    3/1994
JP    08-006490 A    1/1996
(Continued)

OTHER PUBLICATIONS

Search Report dated Sep. 16, 2014, issued by the International Searching Authority in counterpart International Application No. PCT/KR2013/011678 (PCT/ISA/210).
(Continued)

*Primary Examiner* — Claudia Dragoescu
(74) *Attorney, Agent, or Firm* — Sughrue Mion, PLLC

(57) ABSTRACT

A UI providing apparatus is disclosed. The present user interface (UI) providing apparatus comprises: a reception unit for receiving user information using near field communication from a communication device in which the user information is stored; a control unit for configuring a UI so as to respond to information about the type and the degree of a user's disability derived on the basis of the user information; and an output unit for outputting the configured UI.

18 Claims, 16 Drawing Sheets

(51) Int. Cl.
*G06F 3/14* (2006.01)
*G06F 3/16* (2006.01)
*H04B 5/00* (2006.01)
*H04L 12/24* (2006.01)
*H04L 29/08* (2006.01)
*G09B 21/00* (2006.01)
*G16H 40/63* (2018.01)
*H04W 4/80* (2018.01)
*G06F 19/00* (2018.01)

(52) U.S. Cl.
CPC .......... *G09B 21/008* (2013.01); *G16H 40/63* (2018.01); *H04B 5/0031* (2013.01); *H04L 41/22* (2013.01); *H04L 67/10* (2013.01); *H04W 4/80* (2018.02); *G09G 2354/00* (2013.01); *G09G 2380/08* (2013.01)

(56) References Cited

U.S. PATENT DOCUMENTS

| | | | |
|---|---|---|---|
| 6,992,592 | B2 | 1/2006 | Gilfix et al. |
| 7,199,725 | B2 | 4/2007 | Gilfix et al. |
| 2005/0108642 | A1* | 5/2005 | Sinclair, II .......... G06F 9/44505 715/700 |
| 2007/0244825 | A1 | 10/2007 | Semmer et al. |
| 2010/0180238 | A1 | 7/2010 | Lanfermann et al. |
| 2012/0029808 | A1 | 2/2012 | Shin et al. |
| 2012/0054269 | A1 | 3/2012 | Choi et al. |
| 2012/0311019 | A1* | 12/2012 | Raman ............... G06Q 20/3278 709/203 |
| 2015/0121215 | A1* | 4/2015 | Wohlert ............ H04M 1/72591 715/706 |

FOREIGN PATENT DOCUMENTS

| | | |
|---|---|---|
| JP | 09-062870 A | 3/1997 |
| JP | 2000-305746 A | 11/2000 |
| JP | 2001-331846 A | 11/2001 |
| JP | 2004-302832 A | 10/2004 |
| JP | 2009-505264 A | 2/2009 |
| KR | 10-2001-0028791 A | 4/2001 |
| KR | 10-2006-0057152 A | 5/2006 |
| KR | 10-2007-0054315 A | 5/2007 |
| KR | 10-2007-0101481 A | 10/2007 |
| KR | 10-2009-0012388 A | 2/2009 |
| KR | 10-2009-0038078 A | 4/2009 |
| KR | 10-2010-0008278 A | 1/2010 |
| KR | 10-2010-0082513 A | 7/2010 |
| KR | 10-2011-0008505 A | 1/2011 |
| WO | 2012/026642 A1 | 3/2012 |
| WO | 2013/024922 A1 | 2/2013 |

OTHER PUBLICATIONS

Written Opinion dated Sep. 16, 2014, issued by the International Searching Authority in counterpart International Application No. PCT/KR2013/011678 (PCT/ISA/237).

Communication dated Jan. 12, 2019, issued by the Korean Intellectual Property Office in corresponding Korean Application No. 10-2012-0092625.

* cited by examiner

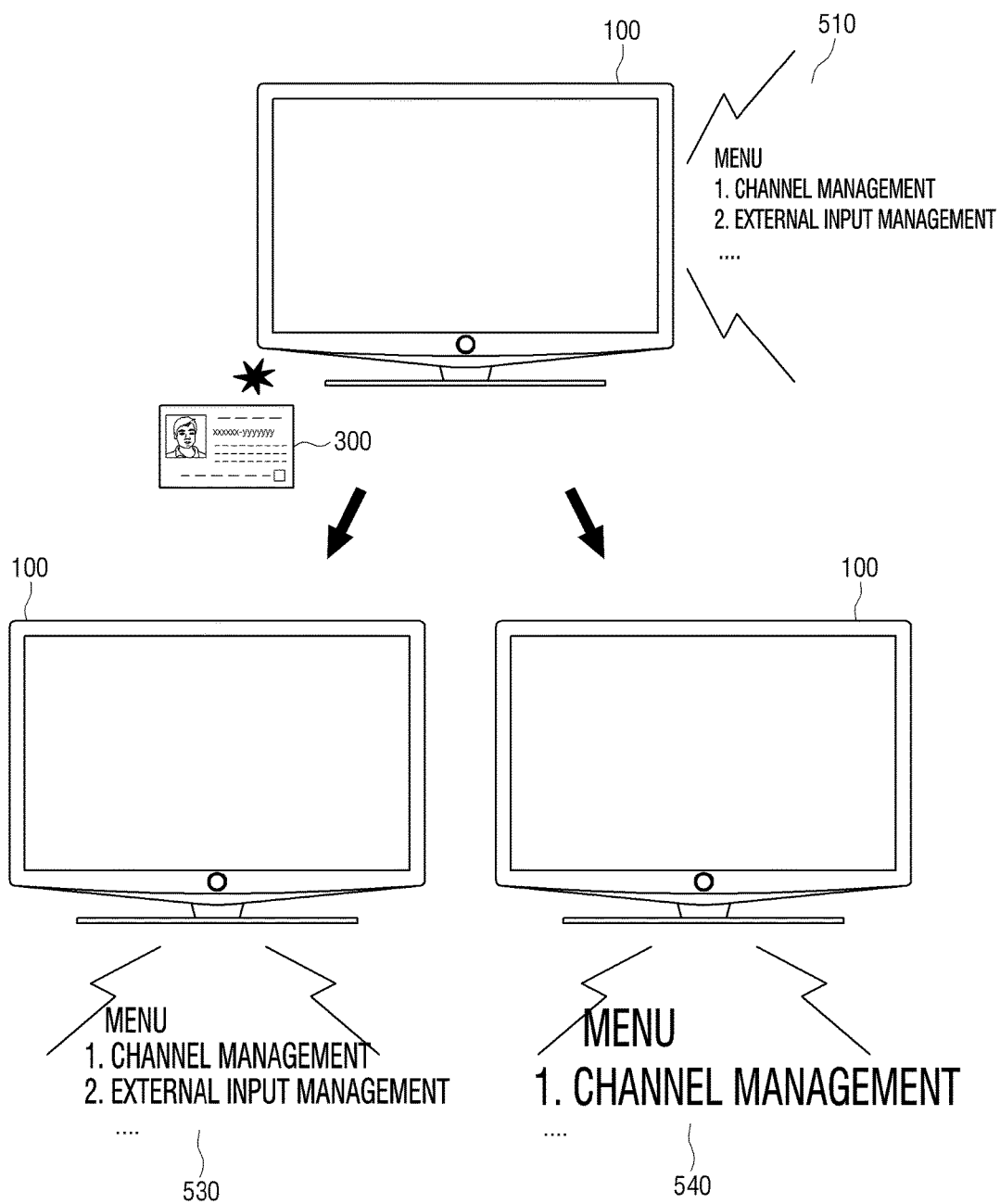

USER INTERFACE (UI) PROVIDING APPARATUS AND UI PROVIDING METHOD THEREOF

CROSS-REFERENCE TO RELATED APPLICATION

This application is a U.S. national stage application under 35 U.S.C. 371 of International Application No. PCT/KR2013/011678, filed on Dec. 16, 2013, in the Korean Intellectual Property Office, the disclosure of which is incorporated herein in its entirety by reference.

BACKGROUND

1. Technical Field

Apparatuses and methods consistent with exemplary embodiments relate to a user interface (UI) providing apparatus and a UI providing method thereof.

2. Description of Related Art

Generally, various electronic apparatuses provide various forms of interfaces mediate communication between the electronic apparatuses and a user. For example, the electronic apparatuses may display various menu screens and receive a user selection on a specific menu.

However, related art electronic apparatuses provide a user of the electronic apparatuses with an interface that is set during manufacture, regardless of whether the user has a disability. Typically, the interface is set for a non-disabled user during manufacture. Thus, a disabled user may have a difficulty in controlling the electronic apparatus through the interface provided from the electronic apparatus.

Accordingly, there is a need for a method for providing the interface in consideration of the disabled user.

SUMMARY

One or more exemplary embodiments provide a user interface (UI) providing apparatus configured to provide a user interface (UI) by considering a disability type and a degree of disability of a user and a UI providing method thereof.

In order to accomplish the above-mentioned objects, a user interface (UI) providing apparatus according to an exemplary embodiment of the present disclosure is provided, including a receiver configured to receive user information through near field wireless communication with a communication device storing the user information, a controller configured to set a UI corresponding to information regarding a disability type and a degree of disability of a user which is obtained based on the user information, and an outputter configured to output the UI as set.

The receiver may include an NFC reader configured to receive the user information through tagging with an NFC tag storing the user information.

The user information may include at least one among a disability type, a degree of disability according to the disability type, and user identification information.

The UI providing apparatus may additionally include a communicator configured to perform communication with a server, in which the controller may control the communicator to transmit the user identification information to the server, and receive the information regarding the disability type and the degree of disability corresponding to the user identification information from the server.

Further, the outputter may include a video outputter configured to output video, and an audio outputter configured to output sound, in which the controller may control the outputter to output at least one among a graphic UI and a voice UI according to a degree of vision impairment when the disability type of the user is vision impairment.

The controller may control the outputter to output the graphic UI corresponding to a pertinent level when the degree of the vision impairment is higher than a preset level, and output the voice UI when the degree of the vision impairment is lower than a preset level.

The outputter may include a video outputter configured to output video, and an audio outputter configured to output sound, in which the controller may control the outputter to output at least one among a graphic UI and a voice UI according to a degree of hearing impairment when the disability type of a user is hearing impairment.

The controller may control the outputter to output the voice UI corresponding to a pertinent level when the degree of hearing impairment is higher than a preset level and output the graphic UI when the degree of hearing impairment is lower than a preset level.

The UI providing apparatus according to an exemplary embodiment of the present disclosure may additionally include a communicator configured to perform communication with the server, in which the controller may control the communicator to transmit the user information to the server when the UI providing apparatus is not storing the information to output the UI corresponding to the disability type and the degree of disability, and receive the UI output information corresponding to the disability type and the degree of disability from the server.

Further, the UI providing apparatus according to an exemplary embodiment may additionally include an inputter configured to receive a user manipulation to modify output state of the UI, in which the controller may control the outputter to output a modified UI when the user information is received after the output state of the UI is modified according to the user manipulation.

According to an exemplary embodiment, the UI providing apparatus may additionally include a communicator configured to perform communication with the server, in which the controller may control the communicator to transmit information regarding a modified UI to the server when the output state of the UI is modified according to the user manipulation.

According to an exemplary embodiment of the present disclosure, a user interface (UI) providing method of a UI providing apparatus is provided, which may include receiving user information through near field wireless communication with a communication device storing the user information, setting a UI corresponding to a disability type and a degree of disability of a user which is obtained based on the user information, and outputting the UI as set.

The receiving may include receiving the user information through tagging with NFC tag storing the user information by using NFC reader.

The user information may include at least one among a disability type, a degree of disability according to the disability type, and user identification information.

According to an exemplary embodiment, the UI providing method may additionally include transmitting the user identification information to the server, and receiving information regarding the disability type and the degree of disability corresponding to the user identification information from the server.

Further, the outputting may include outputting at least one among a graphic UI and a voice UI according to a degree of vision impairment when the disability type of a user is vision impairment.

In this case, the outputting may include outputting a graphic UI corresponding to a pertinent level when the degree of vision impairment is higher than a preset level and output a voice UI when the degree of vision impairment is lower than a preset level.

Further, the outputting may include outputting at least one among a graphic UI and a voice UI according to a degree of hearing impairment when the disability type of a user is hearing impairment.

In this case, the outputting may include outputting a voice UI corresponding to a pertinent level when the degree of hearing impairment is higher than a preset level and output a graphic UI when the degree of hearing impairment is lower than a preset level.

According to an exemplary embodiment, the UI providing method may additionally include transmitting the user information to the server when the UI providing apparatus is not storing information to output a UI corresponding to the disability type and the degree of disability, and receiving the UI output information corresponding to the disability type and the degree of disability from the server.

Further, the outputting may include receiving a user manipulation to modify output state of the UI and outputting the modified UI when the user information is received after the output state of the UI is modified according to the user manipulation.

In this case, the UI providing method according to an exemplary embodiment may additionally include transmitting information regarding the modified UI to the server when the output state of the UI is modified according to the user manipulation.

BRIEF DESCRIPTION OF DRAWINGS

The above and/or other aspects will be more apparent by describing certain example embodiments with reference to the accompanying drawings.

FIGS. 11 to 15B are diagrams illustrating a UI providing method according to exemplary embodiments.

DETAILED DESCRIPTION

Figure 1:
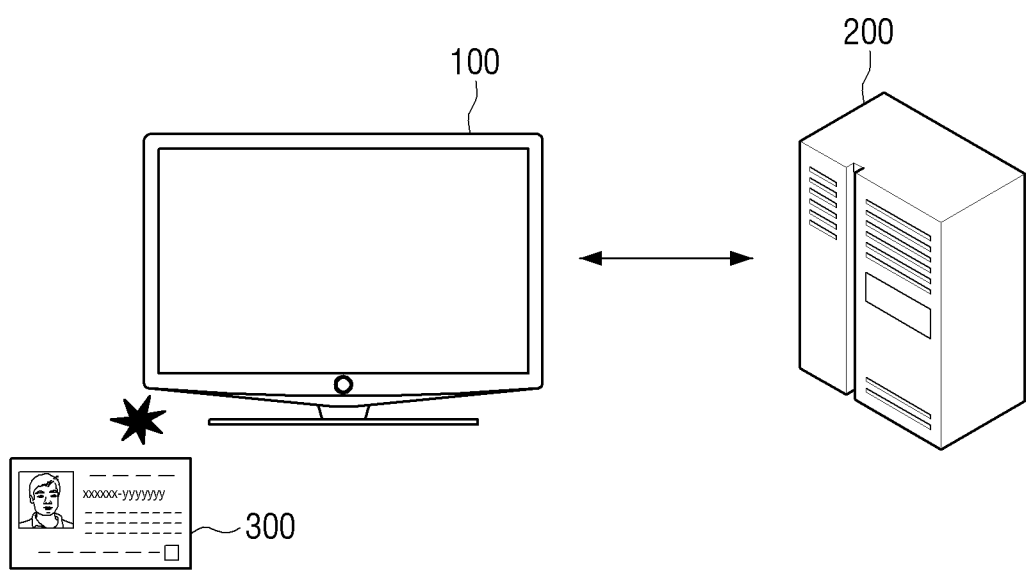
FIG. 1 is a diagram illustrating an example of a user interface (UI) providing system according to an exemplary embodiment.

The inventive concept now will be described more fully hereinafter with reference to the accompanying drawings, in which certain exemplary embodiments are shown. The inventive concept may, however, be embodied in many different forms and should not be construed as limited to the embodiments set forth herein. Rather, these embodiments are provided so that this disclosure will be thorough and complete, and will fully convey the scope of the disclosure to those skilled in the art. In the drawings, the size and relative sizes of layers and regions may be exaggerated for clarity. Like numbers refer to like elements throughout.

FIG. 1 is a diagram illustrating a user interface (UI) providing system according to an exemplary embodiment. Referring to FIG. 1, the UI providing system may include a UI providing apparatus 100, a server 200, and a communication device 300. As illustrated in FIG. 1, the UI providing apparatus 100 may be implemented as a television (TV), although the exemplary embodiments are not limited thereto. The UI providing apparatus 100 may be implemented as various types of electronic apparatuses such as a portable phone, a monitor, a personal digital assistant (PDA), a tablet personal computer (PC), an MP3 player, and so on.

The UI providing apparatus 100 may output a UI corresponding to a disability type and a degree of disability of a user. Herein, the UI may be any interface that can mediate communication between the UI providing apparatus 100 and the user. For example, the UI may include interfaces to control functions provided by the UI providing apparatus 100 or to indicate the functions performed at the UI providing apparatus 100.

Specifically, the UI providing apparatus 100 may output the UI set by default in a normal mode. In an exemplary embodiment, the UI providing apparatus 100 may output a voice UI and/or a graphic UI in a mode that corresponds to a disabled user. Depending on embodiments, the voice UI and the graphic UI may be output together. Herein, the UI set by default in the normal mode may be a graphic UI; however, in an alternative embodiment, the voice UI may be set by default according to functions performed in the UI providing apparatus 100.

To this purpose, the UI providing apparatus 100 may receive user information from the communication device 300. Herein, the user information may include at least one among the disability type, the degree of disability according to the disability type, and user identification information.

Thus, the UI providing apparatus 100 may receive the user information from the communication device 300, and output the UI corresponding to the disability type and/or the degree of disability of a user by using the received user information. Further description will be provided below with reference to FIG. 2.

Figure 2:
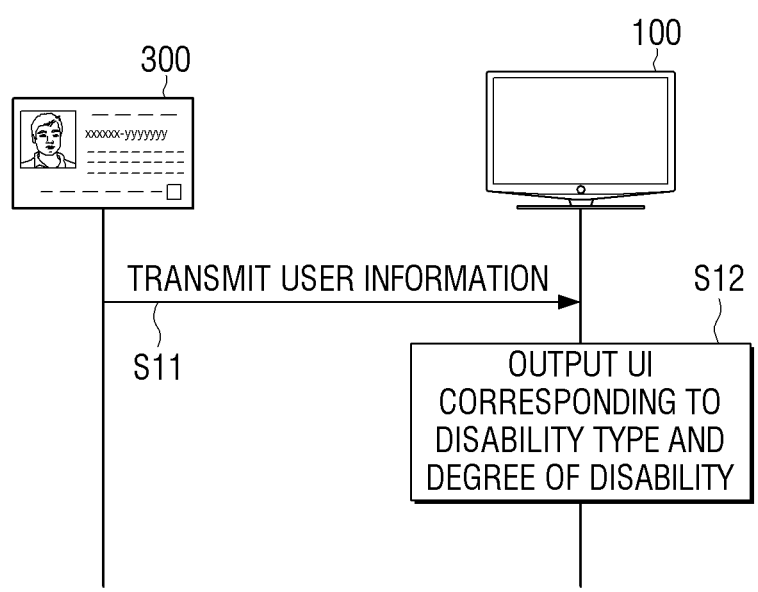
FIG. 2 is a sequence diagram illustrating a UI providing method of a UI providing system according to an exemplary embodiment.

FIG. 2 is a sequence diagram illustrating a UI providing method of the UI providing system according to an exemplary embodiment.

The UI providing apparatus 100 may receive the user information from the communication device 300, at S11. In this case, collecting the user information at the UI providing apparatus 100 may be performed by using various methods.

For example, the UI providing apparatus 100 may collect the user information according to a near field wireless communication method. In this case, the UI providing apparatus 100 may include a near field wireless communication reader. Accordingly, the UI providing apparatus 100 may read data by near-field accessing the communication device 300 including a near field wireless communication tag. Herein, the near-field accessing may indicate a behavior in which at least one of the near field wireless communication tag and a reader moves to the other, and is positioned within a range for communication. Alternatively, the behavior as described above may be referred to as "tagging". When positioned within the range for communication, the near field wireless communication reader may read the data recorded in the near field wireless communication tag.

As an example of the near field wireless communication method, a near field communication (NFC) may be used. The NFC is a non-contact near field wireless communication method using a frequency bandwidth of 13.56 MHz. When NFC technology is used, data may be transmitted and received when a plurality of terminals approach within the near field such as about 10 cm. Further, as another example of the near field wireless communication method, a barcode method, a QR code method, WiFi, Zigbee, and Bluetooth may be used.

The communication device 300 may store the user information, and transmit the user information to the UI providing apparatus 100 according to the various communication methods. For example, the communication device 300 may be implemented in the near field wireless communication tag in which the user information is recorded, and provide the user information in response to tagging on the near field wireless communication reader provided in the UI providing apparatus 100. In this case, the communication device 300 may be implemented as a disabled user card attached with the near field wireless communication tag.

The UI providing apparatus 100 may output the UI corresponding to the disability type and/or the degree of disability of a user by using the user information received from the communication device 300 at S12.

Specifically, the UI providing apparatus 100 may determine the disability type and the degree of disability of a user based on the user information received from the communication device 300, and output at least one of the graphic UI and the voice UI according to the determined disability type and/or degree of disability.

For example, when a user is determined to be visually impaired, the UI providing apparatus 100 may output the graphic UI including UI components having a preset size or more according to the degree of the visual impairment. Herein, the UI components may include a text, an image, a cursor and a pointer. Further, the UI providing apparatus 100 may output the voice UI instead of the graphic UI, or output the graphic UI, including the UI components having a preset size or more, together with the voice UI.

Further, when a user is determined to be hearing impaired, the UI providing apparatus 100 may output the voice UI having a preset volume or more according to the degree of the hearing impairment. Further, the UI providing apparatus 100 may output the graphic UI instead of the voice UI, or output the graphic UI together with the voice UI having a preset volume or more.

To this purpose, the UI providing apparatus 100 may store the information regarding a type of the UI output according to the disability type and the degree of disability of a user, the size of the graphic UI and the output volume size of the voice UI.

Accordingly, the UI providing apparatus 100 may determine the UI type corresponding to the disability type and the degree of disability received from the communication device 300, the size of the graphic UI and the output volume size of the voice UI, and output the corresponding UI.

According to the above exemplary embodiment, the UI providing apparatus 100 may receive the user information from the communication device 300; however, this is merely an example and the exemplary embodiments are not limited thereto.

Specifically, a user may directly input the user information on the UI providing apparatus 100. For example, when the UI providing apparatus 100 includes an input device such as a touch screen, a touch pad, and a button, or is connected to an input device such as a remote controller, a keyboard, and a mouse, a user may directly input his or her disability type, degree of disability, and user identification information through the input device.

For another example, a user may connect the UI providing apparatus 100 to an external storing medium such as a universal serial bus (USB) memory or a memory card, and deliver the user information stored in the external storing medium to the UI providing apparatus 100.

Further, by connecting another terminal apparatus such as a PC, a laptop, a tablet PC, and a portable phone with the UI providing apparatus 100, the user information may be transmitted to the UI providing apparatus 100 from the other terminal apparatus.

When the user information received from the communication device 300 does not include the information regarding the disability type and the degree of disability of a user, the UI providing apparatus 100 may receive corresponding information from the server 200 and output the corresponding UI to the received information. Detailed description thereof will be provided with reference to FIG. 3 below.

Figure 3:
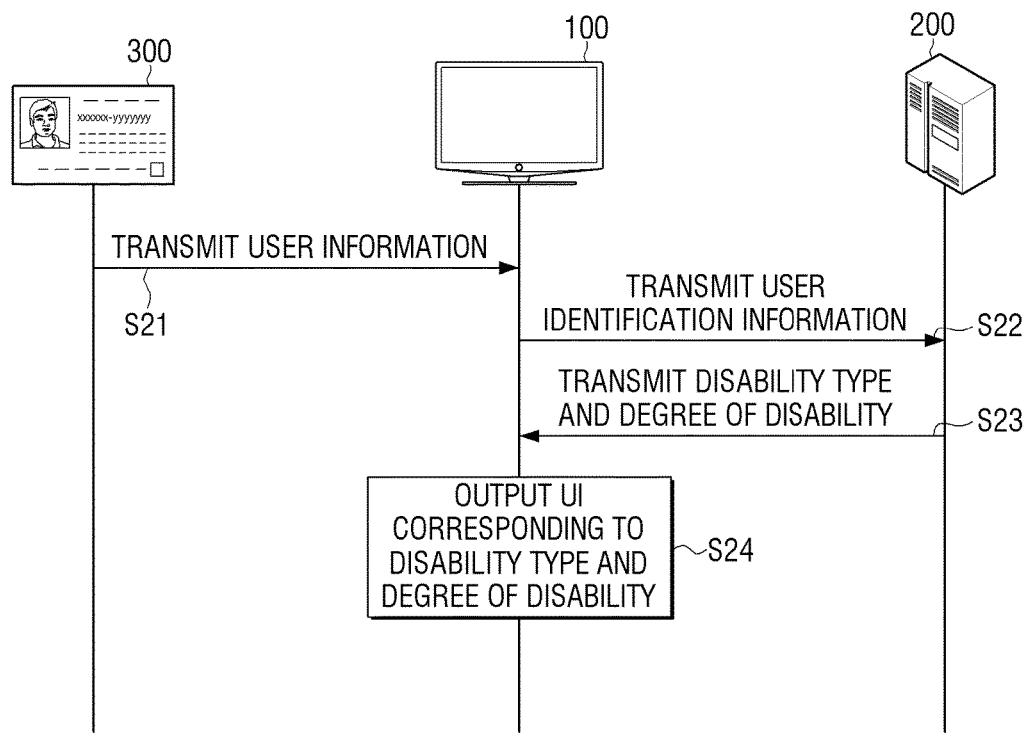
FIG. 3 is a sequence diagram illustrating a UI providing method of a UI providing system according to an exemplary embodiment.

FIG. 3 is a sequence diagram illustrating the UI providing method of the UI providing system according to an exemplary embodiment.

The UI providing apparatus 100 may receive the user information from the communication device 300 storing the user information at S21.

Herein, when the user information received from the communication device 300 does not include the information regarding the disability type and the degree of disability of a user, in other words, when the UI providing apparatus 100 receives only the user identification information from the communication device 300, the UI providing apparatus 100 may transmit the user identification information to the server at S22.

In this case, the server 200 may transmit the information regarding the disability type and the degree of disability corresponding to the user identification information to the UI providing apparatus 100 at S23, and the UI providing apparatus 100 may output the UI corresponding to the disability type and the degree of disability of a user received from the server 200.

To this purpose, the server 200 may store the information regarding the disability type and the degree of disability of a user per user identification information. When the user identification information is received from the UI providing apparatus 100, the server 200 may transmit the information regarding the disability type and the degree of disability which is matched and stored with the received user identification information to the UI providing apparatus 100.

The server 200 may be provided at governmental offices, national and public hospitals and private hospitals, and may perform the communication with the UI providing apparatus 100 through the internet network.

When the UI providing apparatus 100 does not store the information regarding the UI according to the disability type and the degree of disability of a user, the UI providing apparatus 100 may receive pieces of corresponding information from the server 200, and output the UI corresponding to the disability type and the degree of disability of a user by using the received information. Detailed description thereof will be provided with reference to FIG. 4 below.

Figure 4:
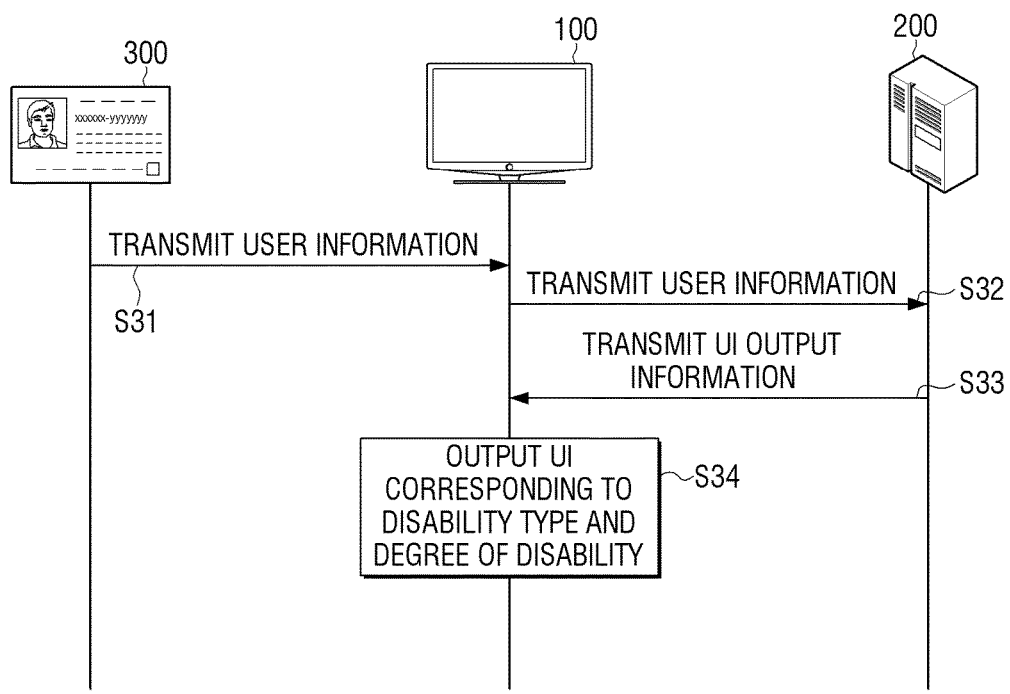
FIG. 4 is a sequence diagram illustrating a UI providing method of a UI providing system according to an exemplary embodiment.

FIG. 4 is a sequence diagram illustrating the UI providing method of the UI providing system according to an exemplary embodiment.

The UI providing apparatus 100 may receive the user information from the communication device 300 storing the user information at S31.

When the UI providing apparatus 100 does not store the information regarding the UI according to the disability type and the degree of disability of a user, the UI providing apparatus 100 may transmit the user information received from the communication device 300 to the server 200 at S32. Herein, the UI providing apparatus 100 may transmit the information regarding the disability type and the degree of disability of a user, transmit the user identification information, or transmit both of the above information to the server 200.

The server 200 may transmit UI output information to the UI providing apparatus 100 so that the UI providing apparatus 100 can output the UI corresponding to the disability type and the degree of disability of a user at S33. Herein, the UI output information may include the information regarding a UI type output in the UI providing apparatus 100 according to the disability type and the degree of disability of a user, a size of the UI in a case where the UI type is the graphic UI, and an output volume size of the UI in a case where the UI type is the voice UI.

Accordingly, the UI providing apparatus 100 may determine the UI type output according to the disability type and the degree of disability of a user, the size of the UI in the case where the UI type is the graphic UI, and the output volume size of the UI in the case where the UI type is the voice UI by using the UI output information received from the server 200, and output the UI corresponding to the disability type and the degree of disability of a user at S34.

The UI providing apparatus 100 may store the information regarding a modified UI when a user manipulation to modify the output state of the UI is input. Next, the UI providing apparatus 100 may output the UI corresponding to the disability type and the degree of disability based on the information regarding the modified UI when the information regarding the disability type and the degree of disability of a user is received. Detailed description thereof will be provided with reference to FIG. 5 below.

Figure 5:
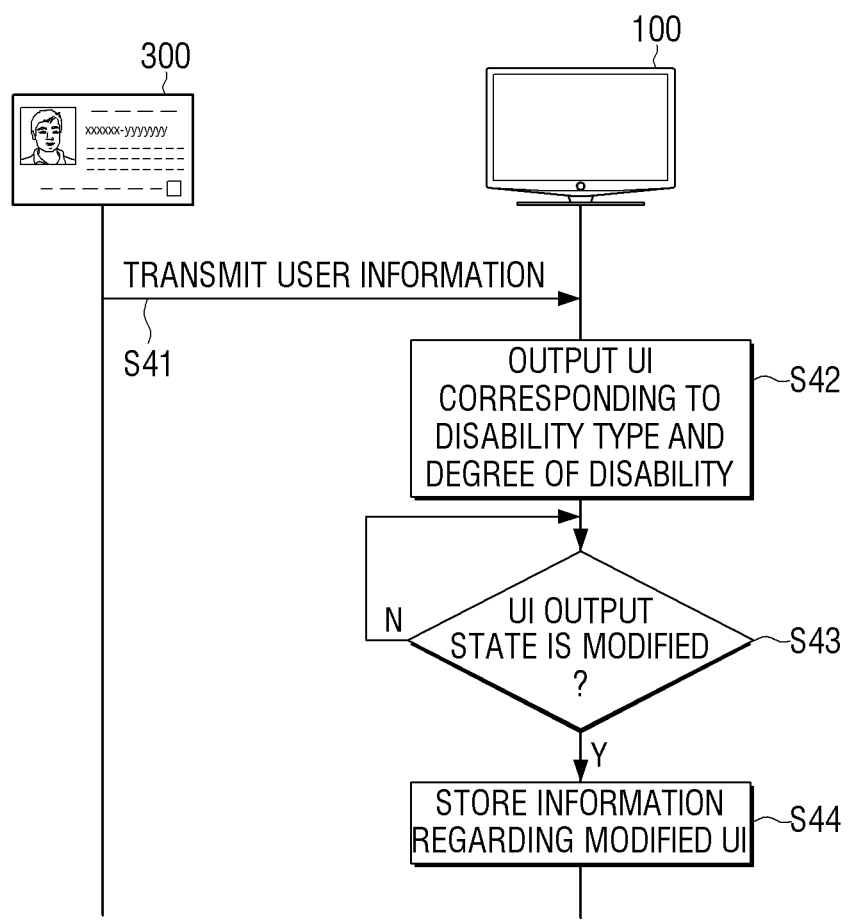
FIG. 5 is a sequence diagram illustrating a UI providing method of a UI providing system according to an exemplary embodiment.

FIG. 5 is a sequence diagram illustrating the UI providing method of the UI providing system according to an exemplary embodiment.

The UI providing apparatus 100 may receive the user information from the communication device 300 storing the user information at S41. Further, the UI providing apparatus 100 may output the UI corresponding to the disability type and the degree of disability of a user by using the user information received from the communication device 300.

The UI providing apparatus 100 may store the information regarding the modified UI at S44 when a user manipulation to modify the output state of the UI is input at S43-Y.

Herein, the UI providing apparatus 100 may match and store the information regarding the modified UI with the disability type and the degree of disability to output the UI in the output state that is modified.

Further, the UI providing apparatus 100 may output the UI corresponding to the disability type and the degree of disability based on the information regarding the modified UI when the information regarding the uniform disability type and degree is received.

For example, while outputting the graphic UI according to the size set for the fourth level visually impaired user, when a user manipulation to adjust the size of the output graphic UI, the UI providing apparatus 100 may store the information regarding the size of the graphic UI which is adjusted according to the user manipulation. In this case, the adjusted size of the graphic UI may be matched and stored with the corresponding disability type and degree of disability, i.e., the fourth level visual impairment. Next, when the information regarding the disability type and the degree of disability corresponding to the fourth level visual impairment is received, the UI providing apparatus 100 may output the graphic UI having the adjusted size.

Although the above describes that the size of the graphic UI is adjusted, this is merely an example. For example, in another exemplary embodiment, in addition to the size of the graphic UI, the output volume size of the voice UI may be also modified, matched and stored with the corresponding disability type and degree of disability.

The exemplary embodiment of FIG. 5 explains a case in which a user manipulation to modify the output state of the UI is input while storing the information regarding the UI type output on the UI providing apparatus 100 according to the disability type and the degree of disability of a user, the size of the graphic UI, and the output volume size of the voice UI.

However, when the UI providing apparatus 100 does not previously store the information to output the UI corresponding to the disability type and the degree of disability of a user, i.e., as in the exemplary embodiment of FIG. 4, the UI providing apparatus 100 may transmit the information regarding the modified UI according to a user manipulation to modify the output state of the UI to the server 200, and the server 200 may store the information regarding the modified UI. Detailed description thereof will be provided with reference to FIG. 6 below.

Figure 6:
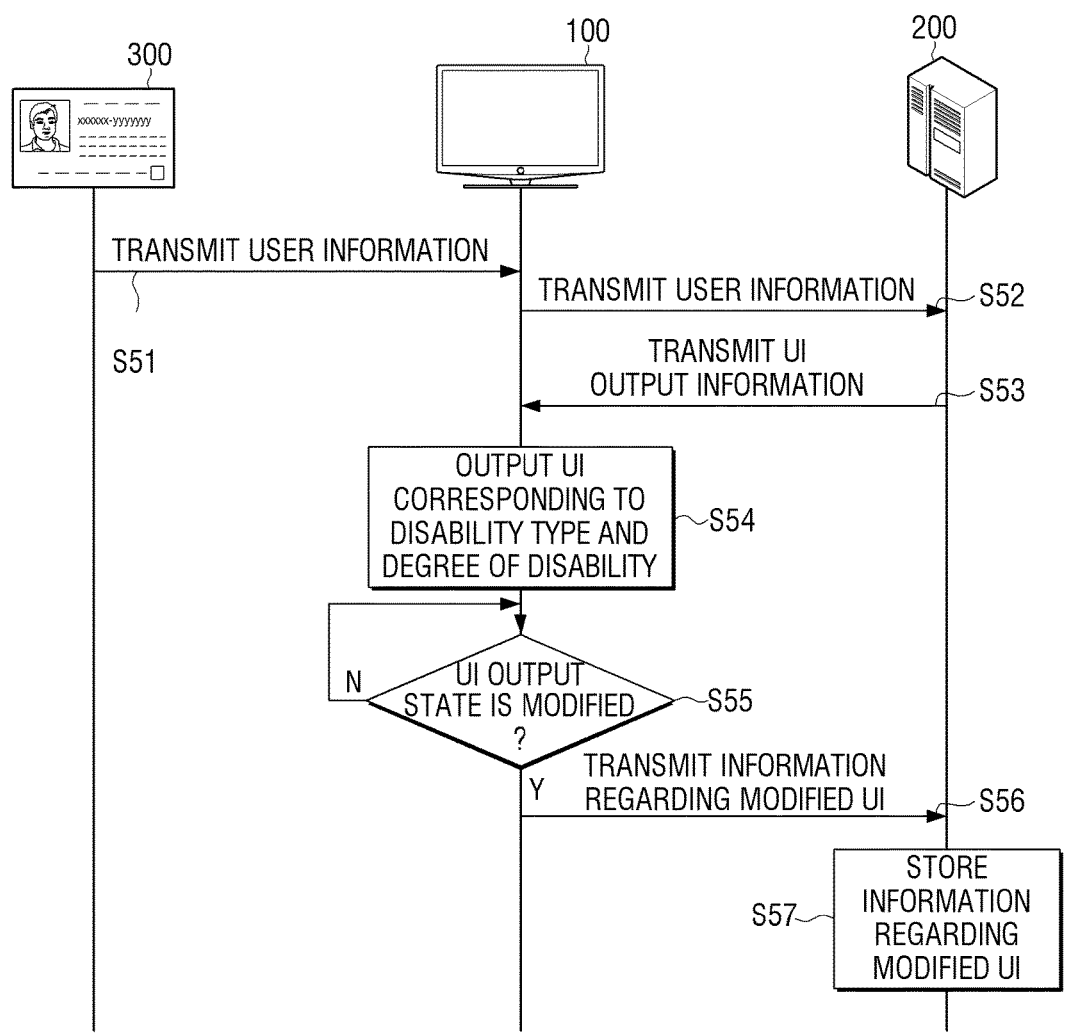
FIG. 6 is a sequence diagram illustrating a UI providing method of a UI providing system according to an exemplary embodiment.

FIG. 6 is a sequence diagram illustrating the UI providing method of the UI providing system according to an exemplary embodiment.

The UI providing apparatus 100 may receive the user information from the communication device 300 storing the user information at S51. When the UI providing apparatus 100 does not store the information to output the UI corresponding to the disability type and the degree of disability of a user, i.e., the information regarding the UI type output according to the disability type and the degree of disability of a user, the size of the graphic UI and the output volume size of the voice UI, the UI providing apparatus 100 may transmit the user information to the server 200 at S52, and receive the UI output information from the server 200 at S53.

Accordingly, the UI providing apparatus 100 may determine the UI type output according to the disability type and the degree of disability of a user the size of the graphic UI, and the output volume size of the voice UI by using the UI output information received from the server 200, and output the UI corresponding to the disability type and the degree of disability of a user at S54.

When a user manipulation to modify the output state of the UI is received at S55-Y, the UI providing apparatus 100 may transmit the information regarding the modified UI to the server 200 at S56. Accordingly, the server 200 may store the information regarding the modified UI received from the UI providing apparatus 100 at S57. Herein, the server 200 may match and store the information regarding the modified UI with the user information.

Further, when the uniform user information is received from the UI providing apparatus 100, the server 200 may transmit the information regarding the modified UI to the UI providing apparatus 100, and the UI providing apparatus 100 may output the UI corresponding to the disability type and the degree of disability based on the information regarding the modified UI.

For example, while outputting the graphic UI according to the size set for the fourth level visually impaired user, when a user manipulation to adjust the size of the output graphic UI is input, the UI providing apparatus 100 may transmit the information regarding the adjusted size of the graphic UI according to the user manipulation to the server 200.

In this case, the server 200 may match and store the adjusted size of the graphic UI with the user information, i.e., the user identification information and the information regarding the disability type and the degree of disability of the corresponding user. Accordingly, when the uniform user information is received from the UI providing apparatus 100, the server 200 may transmit the information regarding the adjusted size of the graphic UI to the UI providing apparatus 100, and the UI providing apparatus 100 may output the graphic UI having the adjusted size.

According to the above various embodiments, the UI providing apparatus 100 may generate and output the UI differentially according to the disability type and the degree of disability of a user. Thus, users having disability can use the UI providing apparatus 100 more easily.

Figure 7:
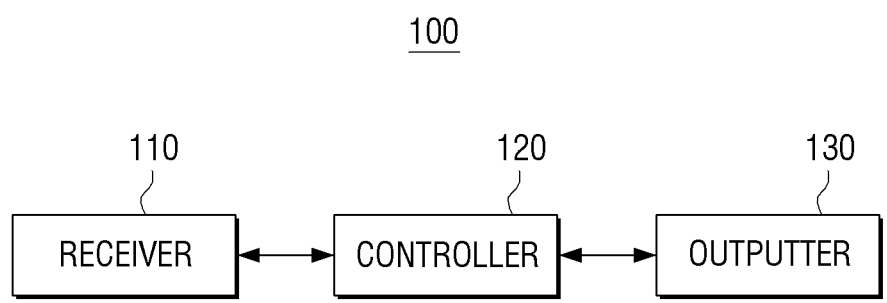
FIG. 7 is a block diagram illustrating a constitution of a UI providing apparatus according to an exemplary embodiment.

FIG. 7 is a block diagram illustrating the UI providing apparatus according to an exemplary embodiment. Referring to FIG. 7, the UI providing apparatus 100 includes a receiver 110, a controller 120 and an outputter 130.

The receiver 110 may receive the user information through the near field wireless communication with the communication device (300 of FIG. 1) storing the user information. To this purpose, the receiver 110 may include NFC reader which receives the user information through tagging with NFC tag storing the user information.

For example, when near-field accessing the communication device 300 attached with the near field wireless communication tag (not shown), the receiver 110 may read the information recorded within the tag and provide the same to the controller 120. The receiver 110 may include a wireless frequency module and antenna coils. The receiver 110 may emit electrical waves through the antenna coils. Accordingly, the electrical currents may be induced according to an electromagnetic induction method in the near field wireless communication tag attached to the communication device 300 positioned within a predetermined distance based on the UI providing apparatus 100. Thus, integrated circuits within the near field wireless communication tag may drive and transmit radio frequency (RF) signals including the stored data. The wireless frequency module within the receiver 110 may receive RF signals through the antenna coils, perform demodulating and decoding regarding the received RF signals, and extract the stored data included in RF signals.

Although the above exemplary embodiment describes that the receiver 110 includes an NFC reader, the receiver 110 may be implemented in any form capable of performing NFC communication.

Further, the receiver 110 may receive the user information from the communication device 300 by using the barcode method, QR code method, WiFi, Zigbee, and Bluetooth which are near field wireless communication methods other than NFC.

The user information may include at least one among the disability type of a user, the degree of disability according to the disability type, and the user identification information. Herein, the disability type may include information regarding the disability types according to features of disability such as visual impairment and hearing impairment, and the degree of disability may include information regarding a disability level per disability type. Further, the user identification information may indicate information for distinguishing a user, and include information such as a name, a resident registration number, and a disability registration number.

Thus, various pieces of information constituting the user information may be stored in each field of the data received from the communication device 300. For example, when the receiver 110 receives the user information according to the NFC communication method, the disability type, the degree of disability and the user identification information may be stored in each field of the data used in the NFC communication method. For example, the information regarding the disability type may be stored in a first data field, the information regarding the degree of disability may be stored in a second data field, and the user identification information may be stored in a third data field.

The controller 120 may set the UI to correspond to the information regarding the disability type and the degree of disability of a user obtained based on the user information. Further, the outputter 130 may output the set UI.

To this purpose, the controller 120 may extract information on the disability type, information the degree of disability and the user identification information in each field of the data received from the receiver 110, and determine the disability type and the degree of disability of a user according to the extracted information. For example, the controller 120 may determine a user to be visually impaired when a bit number corresponding to the information extracted from the first data field is 1, and determine a user to be hearing impaired when the bit number corresponding to the information extracted from the first data field is 0. However, this is merely an example and the information indicating the disability type may be recorded on the data in various other methods.

Further, the controller 120 may determine the UI type output on the UI providing apparatus 100, the size of the graphic UI, and the output volume size of the voice UI according to the disability type and the degree of disability of a user. To this purpose, the UI providing apparatus 100 may store the information regarding the UI type, the size of the graphic UI, and the output volume size of the voice UI which are output according to the disability type and the degree of disability of a user.

For example, the UI providing apparatus 100 may store information regarding the voice UI (i.e., indicating that the output UI type is the voice UI) corresponding to the degree of the vision impairment of a user, which is at a level such that the user cannot recognize any object. Further, the UI providing apparatus 100 may store information regarding the graphic UI or a combination of the graphic UI and the voice UI (i.e., indicating that the output UI type is the graphic UI or the combination of the graphic UI and the voice UI) and the information regarding the size of the graphic UI corresponding to the degree of the vision impairment of a user, which is at a level such that the user can recognize an object.

Further, when the degree of hearing impairment of a user is at a level such that the user cannot hear any sound, the UI providing apparatus 100 may store the information regarding the graphic UI (i.e., indicating that the output UI type is the graphic UI). Further, when the degree of hearing impairment of a user is at a level such that a sound of a preset volume or greater can be heard by the user, the UI providing apparatus 100 may store the information regarding the voice UI or the combination of the voice UI and the graphic UI (i.e., indicating that the output UI type is the voice UI or the combination of the voice UI and the graphic UI) and the information regarding the output volume size of the voice UI.

Further, the UI providing apparatus 100 may store various forms of the graphic UI and the voice UI. Specifically, the UI providing apparatus 100 may store various UIs in the graphic form and/or the voice form such as a UI for receiving a feedback regarding a selected function in the UI providing apparatus 100, a UI for indicating functions performed in the UI providing apparatus 100, and a UI for receiving a user command to control the functions provided in the UI providing apparatus 100.

The controller 120 may determine the UI corresponding to the disability type and the degree of disability of a user based on the information stored in the UI providing apparatus 100, and output the determined UI through the outputter 130.

For example, when the disability type of a user is vision impairment, the controller 120 may control the outputter 130 to output at least one among the graphic UI and the voice UI according to the degree of the disability type. Specifically, the controller 120 may control the outputter 130 to output the graphic UI corresponding to a pertinent level when the degree of the vision impairment is lower than a preset level, and control the outputter 130 to output the voice UI when the degree of the vision impairment is higher than a preset level.

Thus, when a user is determined to be vision impaired, the controller 120 may determine whether the degree of the vision impairment of a user is at a level such that any object cannot be recognized by the user or at a level such that an object can be recognized by the user.

Accordingly, when the degree of the vision impairment of a user is at a level such that any object cannot be recognized by the user, the controller 120 may determine the output UI to be the voice UI, and output the voice UI through the outputter 130. Further, when the degree of the vision impairment of a user at a level such that an object can be recognized by the user, the controller 120 may determine the output UI to be the graphic UI or the combination of the graphic UI and the voice UI, and output the determined UI through the outputter 130.

The voice UI may be provided in various forms according to the degree of the vision impairment.

Specifically, when only the voice UI is output according to degree of the vision impairment of a user, the controller 120 may output the voice UI to receive a user command for controlling the functions provided by the UI providing apparatus 100. In this case, the controller 120 may operate in a voice recognition mode to analyze the user voice input through a microphone (not illustrated) that is provided on the UI providing apparatus 100, and perform the control operation according to the analyzed user voice. For example, when the UI providing apparatus 100 is implemented as a TV, the controller 120 may output the voice UI that speaks "Speak a channel number" to receive a selection of a channel through the outputter 130, and select the channel corresponding to the collected user voice.

Further, the voice UI may be implemented in a form such that a certain text is spoken to receive a user command for controlling the functions provided by the UI providing apparatus 100. For example, the controller 120 may output the voice UI corresponding to the text included in a menu such as "menu, 1. Channel management, 2. External input management, . . . ".

Further, when the voice UI is output together with the graphic UI according to the degree of the vision impairment of a user, the controller 120 may output the voice UI inquiring a feedback regarding the function selected through the graphic UI. Thus, the controller 120 may output a notice sound or a voice indicating whether the function corresponding to the user manipulation is correctly performed. For example, when the menu is selected on the graphic UI according to the user manipulation, the controller 120 may output the voice UI such as "Ding Dong Dang" or "The menu is selected." When the menu that cannot be selected on the graphic UI is selected by a user, the controller 120 may output the voice UI such as "negative" or "The menu cannot be selected." Thus, when the voice UI is output together with the graphic UI, the voice UI may perform a function to assist the user's manipulation on the graphic UI.

Further, the voice UI may be provided to explain the graphic UI. For example, the voice UI may be implemented such that the text included in the graphic UI is spoken. Thus, the controller 120 may output the voice UI corresponding to the graphic UI selected by a user or the text included in the graphic UI selected by a cursor or a highlight menu. For example, when the graphic UI to select Channel 00 is selected by a user, the controller 120 may output the voice UI such as "Channel 00 is selected."

The graphic UI may be provided in various forms according to degree of the vision impairment.

For example, the controller 120 may output the graphic UI including the UI components of a preset size or more according to the degree of the vision impairment of a user. Thus, the controller 120 may output the graphic UI including the UI components having the size that can be recognized by a user according to the degree of the vision impairment of a user. Herein, the UI components may include the text, the cursor, and the image constituting the graphic UI.

Furthermore, the controller 120 may modify the color of the UI components, highlight and output a specific part, or modify and output the marking position and the layout of the UI components.

The graphic UI and the voice UI corresponding to the degree of the vision impairment of a user may be generated by using the various methods. For example, the controller 120 may modify the size, the color, the position, and the layout of the graphic UI set by default in the UI providing apparatus 100, and generate the graphic UI corresponding to the degree of the vision impairment. Further, the corresponding graphic UI and voice UI may be previously stored per degree of vision impairment in the UI providing apparatus 100, or received from the server 200.

For another example, the controller 120 may control the outputter 130 to output at least one among the graphic UI and the voice UI according to the degree of hearing impairment when the disability type of a user is hearing impairment. Specifically, when the degree of hearing impairment is lower than a preset level, the controller 120 may control so that the voice UI corresponding to a pertinent level is output. Further, when the degree of hearing impairment is higher than a preset level, the controller 120 may control to output the graphic UI.

Thus, when a user is determined to be hearing-impaired, the controller 120 may determine whether the degree of hearing impairment of a user is at a level such that any sound cannot be heard by the user or a sound of a preset level or greater can be heard by the user.

Accordingly, when the degree of hearing impairment of a user is at a level such that any sound cannot be heard by the user, the controller 120 may determine the graphic UI to be output and output the graphic UI through the outputter 130. Further, when the degree of hearing impairment of a user is at a level such that a sound of a preset level or greater can be heard by the user, the controller 120 may determine the voice UI or the combination of the graphic UI and the voice UI to be output, and output the determined UI through the outputter 130.

The controller 120 may output the graphic UI set by default in the UI providing apparatus 100. However, the voice UI may be provided in various forms according to the degree of hearing impairment.

For example, when the voice UI is output according to the degree of hearing impairment of a user, the controller 120 may output the voice UI having a volume of a preset level or more according to the degree of hearing impairment of a user. Thus, the controller 120 may output the voice UI having a volume that can be recognized by the user according to the degree of hearing impairment of a hearing-impaired user.

In this case, the voice UI may be a voice UI to receive a user command for controlling the functions provided by the UI providing apparatus 100, a voice UI to receive a feedback regarding the selected function through the graphic UI, and a voice UI to explain about the graphic UI.

The voice UI corresponding to the degree of hearing impairment of a user may be generated by using various methods. For example, the controller 120 may generate the voice UI having a volume size that can be recognized according to the degree of hearing impairment of a user by amplifying a sound of the voice UI set by default in the UI providing apparatus 100. Further, the voice UI may be previously stored per degree of hearing impairment in the UI providing apparatus 100 or received from the server 200.

Although the above exemplary embodiment describes that a user is vision-impaired or hearing-impaired, this is merely an example. The UI providing apparatus 100 may output the UI differentially for a user having another type of the disability. For example, when a user is determined to be impaired such that the user cannot freely use the body, e.g., physical disability, the controller 120 may output the voice UI instead of the graphic UI set by default.

Figure 8:
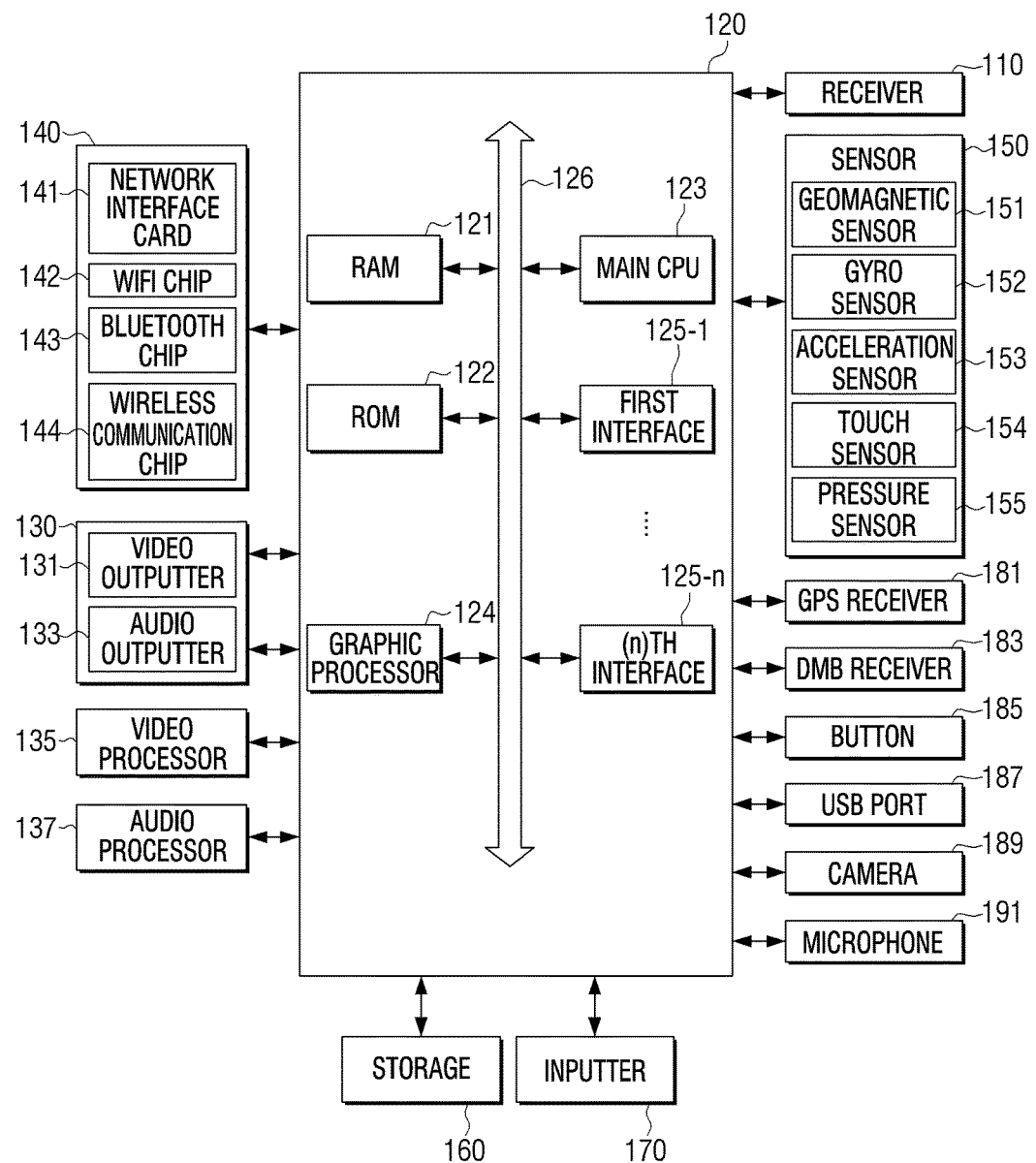
FIG. 8 is a block diagram illustrating a UI providing apparatus according to an exemplary embodiment.

FIG. 8 is a block diagram illustrating the detailed constitution of the UI providing apparatus according to an exemplary embodiment. Referring to FIG. 8, the UI providing apparatus 100 may include a video outputter 131, an audio outputter 133, a video processor 135, an audio processor 137, a communicator 140, a sensor 150, a storage 160, an inputter 170, a global positioning system (GPS) receiver 181, a digital multimedia broadcasting (DMB) receiver 183, a button 185, a USB port 187, a camera 189, and the microphone 191 in addition to the elements illustrated in FIG. 7.

The storage 160 may store various pieces of information.

In exemplary embodiment, the storage 160 may store the information to output the UI corresponding to the disability type and the degree of disability of a user. For example, the storage 160 may store the information regarding the UI type that is to be output corresponding to the disability type and the degree of disability of a user, the size of the graphic UI, and the output volume size of the voice UI.

Further, the storage 160 may store UIs in various forms. For example, the storage 160 may store the graphic UI and the voice UI that are set by default in the UI providing apparatus 100, and store the graphic UI and the voice UI corresponding to the disability type and the degree of disability of a user.

In this case, the corresponding UIs may include various pieces of information such as a UI to receive feedbacks regarding the function selected according to a user manipulation, a UI to indicate the function performed in the UI providing apparatus 100, and a UI to receive a user command to control the function provided in the UI providing apparatus 100.

To this purpose, the storage 160 may store at least one type of the storing media among the flash memory type, the hard disk type, the multimedia card micro type, the memory in the card type (e.g., secure digital (SD) or extreme digital (XD) memory), a random access memory (RAM), and a read only memory (ROM).

Accordingly, the controller 120 may control so that the UI corresponding to the disability type and the degree of disability of a user is output, by using various pieces of the information stored in the storage 160.

For example, the controller 120 may read and signal-process the graphic UI and the voice UI corresponding to the disability type and the degree of disability of a user from the storage 160, and output the signal-processed UI through the outputter 130. Further, the controller 120 may modify the size of the UI components included in the graphic UI set by default or amplify a sound of the voice UI, and output the modified UI through the outputter 130.

The communicator 140 is provided to perform the communication with the server (200 of FIG. 2). For example, the communicator 140 may perform the communication with the server 200 through an internet network by including a network interface card 141.

The controller 120 may control the communicator 140 to transmit the user identification information to the server 200 and to receive the information regarding the disability type and the degree of disability corresponding to the user identification information from the server 200. Thus, when there is no information regarding the disability type and the degree of disability on the data received from the communication device 300 through the receiver 110, the controller 120 may transmit the user identification information to the server 200, and receive the information regarding the disability type and the degree of disability corresponding to the user identification information from the server 200.

Accordingly, the controller 120 may determine the UI type to be output corresponding to the disability type and the degree of disability of a user received from the server 200, the size of the graphic UI, and the output volume size of the voice UI, and output the UI corresponding to the disability type and the degree of disability of a user through the outputter 130.

Further, when the UI providing apparatus 100 does not store the information to output the UI corresponding to the disability type and the degree of disability, the controller 120 may control the communicator 140 to transmit the user information to the server 200, and receive the UI output information corresponding to the disability type and the degree of disability from the server 200. Thus, when the storage 160 does not store the UI type to be output corresponding to the disability type and the degree of disability of a user, the size of the graphic UI, and the output volume size of the voice UI, the controller 120 may receive the corresponding information from the server 200.

Accordingly, the UI output information received from the server 200 may include the information regarding the UI type output in the UI providing apparatus 100 according to the disability type and the degree of disability, the size of the graphic UI, and the output volume size of the voice UI.

For example, when a user is fourth level visually impaired, the UI output information received from the server 200 may include the information indicating that the graphic UI provided to the fourth level visually impaired user is a graphic UI and the size of the UI components included in the corresponding graphic UI.

Therefore, the controller 120 may determine the UI type corresponding to the disability type and the degree of disability of a user, the size of the graphic UI and the output volume size of the voice UI based on the UI output information received from the server 200, and output the UI corresponding to the disability type and the degree of disability of a user through the outputter 130.

The communicator 140 may include a WiFi chip 142, a Bluetooth chip 143, and a wireless communication chip 144.

The WiFi chip 142 and the Bluetooth chip 143 may perform communication according to WiFi and Bluetooth, respectively. For example, when the WiFi chip 142 or the Bluetooth chip 143 is used, various pieces of connecting information such as a service set identifier (SSID) and a session key may be first transmitted and received, the communication may be connected by using the above information, and various pieces of information may be transmitted and received.

The wireless communication chip 144 indicates a chip to perform the communication according to various communication standards such as Institute of Electrical and Electronic Engineers (IEEE) standard, Zigbee, $3^{rd}$ generation (3G), $3^{rd}$ generation partnership project (GPP), and long term evolution (LTE).

Accordingly, the communicator 140 may transmit and receive various pieces of information by performing the wireless communication with external devices according to various communication methods.

The sensor 150 may include a geomagnetic sensor 151, a gyro sensor 152, an acceleration sensor 153, a touch sensor 154, and a pressure sensor 155. The sensor 150 may sense various user manipulation on the UI providing apparatus 100 such as touching, rotating, tilting, and pressing.

The geomagnetic sensor 151 is sensor to sense rotating and/or a moving direction of the UI providing apparatus 100. The gyro sensor 152 is sensor to sense a rotating angle of the UI providing apparatus 100. The geomagnetic sensor 151 and the gyro sensor 152 may be both included in the UI providing apparatus 100; however, even when only one of the geomagnetic sensor 151 and the gyro sensor 152 is provided, the UI providing apparatus 100 may sense rotating thereof.

The acceleration sensor 153 is a sensor to sense a tilting degree of the UI providing apparatus 100.

The touch sensor 154 may be implemented as a capacitive or resistive type. The capacitive type involves a method which uses a dielectric material coated on the surface of the video outputter 131, to sense micro electricity excited by the user's body when the body part of a user touches on the surface of the video outputter 131 and calculate a touch coordinate. The resistive type involves a method which uses upper and lower electrode plates to sense electrical current flow at a contact between the upper and the lower plate when a user touches the screen and calculate a touch coordinate. As described above, the touch sensor 154 may be implemented in various forms including the capacitive type and the resistive type.

The pressure sensor 155 may sense the amount of the pressure applied to the UI providing apparatus 100 when a user inputs a touch manipulation, and provide the sensed result to the controller 120. The pressure sensor 155 may include a piezo film included within the video outputter 131 to output an electrical signal corresponding to the amount of the pressure. FIG. 5 illustrates that the touch sensor 154 and the pressure sensor 155 are separate components; however, when the touch sensor 154 is implemented as a resistive touch sensor, the resistive touch sensor may perform a role of the pressure sensor 155.

The controller 120 may analyze the various signals sensed by the sensor 150, confirm the intention of a user, and perform the operation corresponding to the intention.

For example, the controller 120 may perform the control operation according to various inputting methods such as touch inputting, motion inputting, voice inputting, button inputting, and so on. The touch input may include various gestures such as a single touch, tap, touch and hold, move, flick, drag and drop, pinch in, pinch out, and so on.

For example, the controller 120 may generate and display an application execution screen by implementing the application stored in the storage 160, and reproduce various contents stored in the storage 160. Herein, the content may indicate various multimedia content such as an image, a text, a picture, a video, and so on. Further, the controller 120 may receive the content by performing the communication with external devices through the communicator 140.

Further, the controller 120 may modify the display direction of the content displayed on the outputter 130 based on the rotation of the UI providing apparatus 100. For example, when the UI providing apparatus 100 rotates toward the left direction by 90°, the controller 120 may control so that the content that is rotated toward the left direction by 90° is displayed.

The inputter 170 may receive various user manipulation. The controller 120 may perform the operation corresponding to the various user manipulation input through the inputter 170. For example, when a user manipulation to turn on the UI providing apparatus 100 is input through the inputter 170, the controller 120 may provide electrical power to each element of the UI providing apparatus 100.

To this purpose, the inputter 170 may be implemented as a remote controller receiver or an input port to receive a user manipulation from an input device such as a remote controller, a keyboard, and a mouse, or may be implemented as a touch screen or touch pad together with the outputter 130.

Further, the inputter 170 may receive a user manipulation to modify the output state of the UI. In this case, the controller 120 may control the outputter 130 to output the UI in the modified output state when the user information is received after the output state of the UI is modified according to a user manipulation.

For example, the controller 130 may display the UI screen to modify the output state of the UI according to a user manipulation through the outputter 130. Further, when a user manipulation to modify the size of the UI components included in the graphic UI is input on the UI screen or when a user manipulation to modify the output volume size of the voice UI is input, the controller 120 may store the information regarding the modified UI according to the user manipulation in the storage 160.

In this case, the controller 120 may match and store the information regarding the modified UI with the disability type and the degree of disability set to output the UI before the output state is modified. Accordingly, when the information regarding the uniform disability type and degree is received, the controller 120 may output at least one among the graphic UI in which the size is modified and the voice UI in which the output volume size is modified.

For example, while outputting the graphic UI according to the size set for the fourth level visually impaired user, when a user manipulation to adjust the size of the output graphic UI is input, the controller 120 may store the information regarding the adjusted size of the graphic UI according to the user manipulation in the storage 160. In this case, the controller 120 may match and store the adjusted size of the graphic UI with the corresponding disability type and degree, i.e., with the fourth level visually impaired user. Accordingly, when the information regarding the disability type and degree corresponding to the fourth level visually impaired user is received, the controller 120 may output the graphic UI having the adjusted size through the outputter 130.

Although the above exemplary embodiment describes that the information regarding the modified UI may be matched and stored with the disability type and the degree of disability, this is merely an example. Thus, the controller 120 may normalize the information regarding the UI corresponding to the disability type and the degree of disability and the information regarding the modified UI, match and store the information regarding the normalized UI with the disability type and the degree of disability. In this case, when the information regarding the uniform disability type and degree is received, the controller 120 may output the UI corresponding to the disability type and the degree of disability based on the information regarding the normalized UI.

According to the above exemplary embodiment, the controller 120 may normalize the size set for the providing of the fourth level visually impaired user and the size adjusted by a user manipulation, and store the information regarding the normalized size of the graphic UI in the storage 160. In this case, the controller 120 may match and store the normalized size of the graphic UI with the corresponding disability type and degree. Thus, when the size set for the providing of the fourth level visually impaired user is 7 and when the size adjusted by a user manipulation is 9, the controller 120 may match and store the normalized value, i.e., 8, with the fourth level visually impaired user.

Accordingly, when the information regarding the disability type and the degree of disability corresponding to the fourth level visually impaired user is received, the controller 120 may output the graphic UI having the normalized size through the outputter 130.

As described above, when the storage 160 does not store the information to output the UI corresponding to the disability type and the degree of disability, the controller 120 may output the UI corresponding to the disability type and the degree of disability of a user by using the UI output information received from the server 200.

In this case, when the output state of the UI is modified according to a user manipulation, the controller 120 may control the communicator 140 to transmit the information regarding the modified UI to the server 200. Herein, the server 200 may match and store the information regarding the modified UI with the user information. When the uniform user information is received through the receiver 110, the controller 120 may transmit the user information to the server 200, and the server 200 may transmit the UI output information that is matched and stored with the user information, i.e., the information regarding the modified UI, to the UI providing apparatus 100. Accordingly, the controller 120 may output the UI corresponding to the disability type and the degree of disability of a user based on the information regarding the modified UI.

For example, while outputting the graphic UI according to the size set for the fourth level visually impaired user, when a user manipulation to adjust the size of the output graphic UI is input, the controller 120 may transmit the information regarding the adjusted size of the graphic UI according to a user manipulation to the server 200. Next, when the uniform user information is received, the controller 120 may transmit the user information to the server 200. Further, the controller 120 may receive the information regarding the adjusted size of the graphic UI from the server 200, and output the graphic UI having the adjusted size through the outputter 130.

Although the above exemplary embodiment describes that the information regarding the modified UI is stored in the server 200, this is merely an example. Thus, the server 200 may normalize the UI output information corresponding to the disability type and the degree of disability and the information regarding the modified UI, match and store the information regarding the normalized UI with the user information. Accordingly, when the uniform user information is received, the server 200 may transmit the information regarding the normalized UI to the UI providing apparatus 100. Further, the controller 120 may output the UI corresponding to the disability type and the degree of disability of a user by using the information regarding the normalized UI.

The GPS receiver 181 is provided to receive a GPS signal from a GPS satellite, and calculate the current position of the UI providing apparatus 100.

The DMB receiver 183 is provided to receive and process a DMB signal.

The video processor 135 is provided to perform processing regarding video data. The video processor 135 may perform various image processing such as decoding, scaling, noise filtering, frame rate converting, and resolution converting regarding the video data. Specifically, the video processor 135 may process the graphic UI corresponding to the disability type and the degree of disability into a form that can be output through the video outputter 131. Specifically, the video processor 135 may modify and process the sizes of the graphic UI stored as default and the UI components constituting the corresponding graphic UI into a form that can be output in the video outputter 131.

The audio processor 137 is provided to perform processing regarding the audio data. The audio processor 137 may perform various processing such as decoding, amplifying, and noise filtering regarding the audio data. Specifically, the audio processor 137 may process the voice UI corresponding to the disability type and the degree of disability into a form that can be output through the audio outputter 133. Further, the audio processor 137 may control amplifying of the voice UI stored as default and the corresponding voice UI, and the outputting the amplified voice UI through the audio outputter 133.

The outputter 130 includes the video outputter 131 for outputting the video and the audio outputter 133 for outputting the voice.

The video outputter 131 may display the video data processed in the video processor 135 in the video form. To this purpose, the video outputter 131 may be implemented as various forms such as a liquid crystal display (LCD), an organic light emitting display (OLED) or a plasma display panel (PDP).

The audio outputter 133 may output the audio data processed in the audio processor 137 in the audio form. Further, the audio outputter 133 may output various notice sounds and voice messages. To this purpose, the audio outputter 133 may be implemented as an output port such as a jack or a speaker.

The controller 120 may output various screens or objects through the video outputter 131 and the audio outputter 133. For example, the controller 120 may signal-process the various images, texts, pictures, and videos stored in the storage 160 in a form that can be processed through the video processor 135 and the audio processor 137, and output a result of the signal-processing through the video outputter 131 and the audio outputter 133.

Further, the controller 120 may display the screen to receive various user commands through the video outputter 131. Specifically, the controller 120 may display the menu screen to modify the output state of the UI according to a user manipulation through the video outputter 131.

Further, the controller 120 may output the graphic UI corresponding to the disability type and the degree of disability of a user through the video outputter 131, and output the voice UI corresponding to the disability type and the degree of disability of a user through the audio outputter 133.

The button 185 may be various types of buttons such as a mechanical button, a touch pad, and a wheel formed on an arbitrary area of the front surface, the side surface, and the rear surface of the exterior main body of the UI providing apparatus 100. Various user manipulations to control the operation of the UI providing apparatus 100 such as commands to turn on and off the electrical power may be received through the button 185.

The USB port 187 may indicate a port that can be connected to a USB memory and a USB connector. Various contents may be received from and transmitted to an external device through the USB port.

The camera 189 is provided to photograph a still image or video according to controlling of a user. The camera 189 may be implemented in a plural number including, for example, a front camera and a back camera.

The microphone 191 is provided to receive a user voice or other sounds and convert the same into the audio data. The controller 120 may use the user voice input through the microphone 191 during a call, or convert the user voice into the audio data and store the converted user voice in the storage 160.

The camera 189 may perform the control operation according to the user voice input through the microphone 191 or the user motion recognized by the camera 189 when the camera 189 and the microphone 191 are provided. Thus, the UI providing apparatus 100 may operate in the motion control mode or the voice control mode.

For example, when operating in the motion control mode, the controller 120 may photograph a user by activating the camera 189, and perform the control operation such as turning on or off the electrical power by tracking the change in the user motion. Further, when operating in the voice control mode, the controller 120 may operate in the voice recognition mode which analyzes the user voice input through the microphone, and performs the control operation according to the analyzed user voice.

Additionally, various external input ports to connect with various external components such as a headset, a mouse or a local area network (LAN) may be further included.

The above described operation of the controller 120 may be performed by the program stored in the storage 160. The storage 160 may store various data such as operation system (O/S) software to drive the UI providing apparatus 100, various applications, various data input or set during the implementation of the applications, and content.

The controller 120 may generally control the operation of the UI providing apparatus 100 by using the various programs stored in the storage 160.

The controller 120 may include a RAM 121, a ROM 122, a main central processing unit (CPU) 123, a graphic processor 124, a first to an n-th interfaces 125-1~125-n, and a bus 126.

The RAM 121, the ROM 122, the main CPU 123, the graphic processor 124, and the first to the n-th interfaces 125-1~125-n may be connected to each other through the bus 136.

The first to the n-th interfaces 125-1 to 125-n may be connected to the various elements described above. One of the interfaces may be a network interface connected to an external device through the network.

The main CPU 123 may access the storage 160 and perform booting by using the stored O/S in the storage 160. Further, the main CPU 123 may perform various operation by using the various programs, content and data stored in the storage 160.

The ROM 122 may store a command set for the system booting. When a turn-on command is input and the electrical power is provided, the main CPU 123 may copy the stored O/S in the storage 160 to the RAM 121 according to the command stored in the ROM 122, and boot the system by implementing O/S. When the booting completes, the main CPU 123 may copy the various application programs stored in the storage 160 to the RAM 121, and perform various operation by implementing the copied application programs in the RAM 121.

The graphic processor 124 may constitute various screens according to the controlling of the main CPU 123. Specifically, the graphic processor 124 may calculate display state values regarding the screen. The display state values may indicate feature values indicating the coordinate values in which objects are to be marked on the screen, the shape, the size and the color of the object. The graphic processor 124 may perform rendering based on the coordinate values and constitute the screen when the display state values are calculated.

Because the constitution of the UI providing apparatus 100 illustrated in FIG. 8 is merely an example, some elements of FIG. 8 may be omitted or modified and other new elements may be further added according to an exemplary embodiment.

As described above, the controller 120 may perform various operation by implementing the programs stored in the storage 160.

Figure 9:
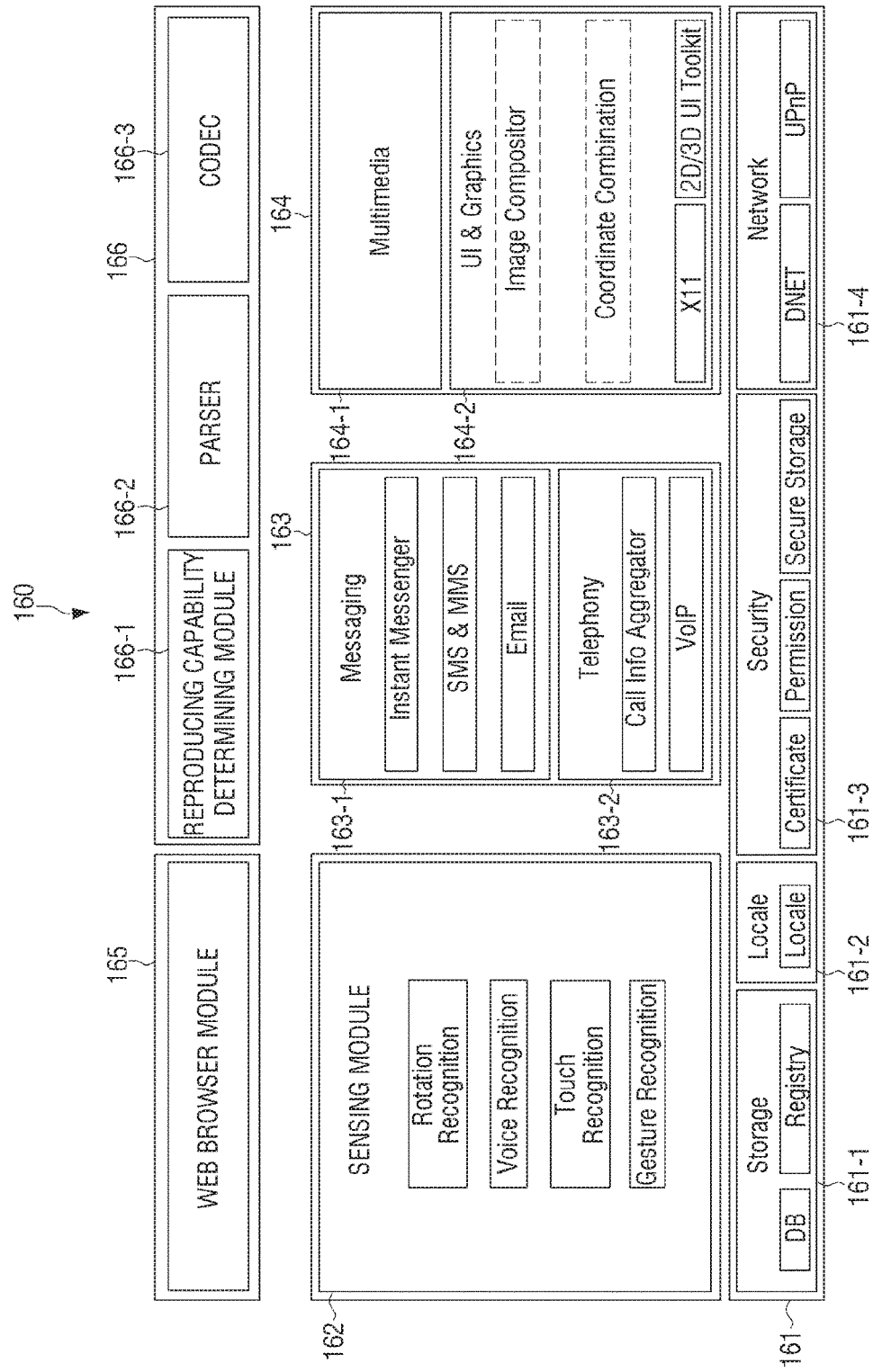
FIG. 9 is a diagram illustrating a hierarchy of software stored in a storage of a UI providing apparatus according to an exemplary embodiment.

FIG. 9 is a diagram illustrating the hierarchy of the software stored in the storage. Referring to FIG. 9, the storage 160 may include a base module 161, a sensing module 162, a communicating module 163, a presentation module 164, a web browser module 165, and a content processing module 166.

The base module 161 refers to a basic module to process the signal delivered from each hardware provided in the UI providing apparatus 100 and deliver the processed signal to upper layer modules.

The base module 161 may include a storage module 161-1, a position base module 161-2, a security module 161-3, and a network module 161-4.

The storage module 161-1 is a program module which manages a DB or a registry. The main CPU 123 may access to DB within the storage 160 by using the storage module 161-1, and read various data. The position base module 161-2 is a program module which supports a position base service by interoperating with various hardware such as a GPS chip. The security module 161-3 is a program module which supports the hardware certification, the request permission, and the secure storage. The network module 161-4 is a module which supports the network connection, and may include DNET module and UPnP module.

The sensing module 162 is a module which manages the information regarding an external input and/or an external device and uses the information regarding the external input and/or the external device. The sensing module 162 includes a rotation recognition module, a voice recognition module, a touch recognition module, and a gesture recognition module. The rotation recognition module is a program which calculates a rotating angle and a rotating direction by using the sensing values sensed by the sensor such as the geomagnetic sensor 151 and the gyro sensor 152. The voice recognition module is a program which analyzes the voice signals collected in the microphone 191 and extract the user voice. The touch recognition module is a program which extracts touch coordinate values by using the sensing values sensed by the touch sensor 154, and the gesture recognition module is a program which recognizes the user gesture by analyzing an image photographed by the camera 189.

The communicating module 163 is a module to perform communication with an external device. The communicating module 163 may include a messaging module 163-1 such as a messenger program, a short message service (SMS) and/or multimedia message service (MMS) program, and an e-mail program and a call module 163-2 such as a call info aggregator program module and a VoIP module.

The presentation module 164 is a module to constitute the display screen. The presentation module 164 may include a multimedia module 164-1 which reproduces and outputs the content, and a UI and graphic module 164-2 which performs the processing regarding the UI and the graphic. The multimedia module 164-1 may include a player module, a camcorder module, and a sound processing module. Accordingly, the multimedia module 164-1 may reproduce various contents, generate and reproduce screens and sounds. The UI and graphic module 164-2 may include an image compositor module which combines images, a coordinate combination module which combines and generate coordinate values on the screen in which images will be displayed, an X11 module which receives various events from the hardware, and a two dimensional/three dimensional (2D/3D) UI toolkit which provides tools to provide the UI in a 2D or 3D form.

The web browser module 165 refers to a module which performs the web browsing and accesses to the web server. The web browser module 165 may include various modules such as a web view module constituting web pages, a download agent module performing the downloading, a bookmark module, and a webkit module.

The content processing module 166 refers to software to process the content stored in the storage 160. The content processing module 166 may include a reproducing capability determining module 166-1, a parser 166-2, and a codec 166-3. The reproducing capability determining module 166-1 is a program which operates with the algorithms comparing the reproducing capability information with the content features. The parser 166-2 and the codec 166-3 are software provided to the video processor 135 for content processing. The parser 166-2 may be implemented as software only, and the codec 166-3 may be implemented as software or hardware.

Various application modules such as a navigation service module and a game module may be further included in the software stored in the storage.

Some of the various program modules illustrated in FIG. 9 may be omitted or modified and other modules may be added according to the type and the feature of the UI providing apparatus 100. For example, when the UI providing apparatus 100 is a smart phone, an electronic book application, a game application and other utility programs may be further included. Further, some of the program modules in FIG. 9 may be omitted when the UI providing apparatus is a smart phone.

Figure 10:
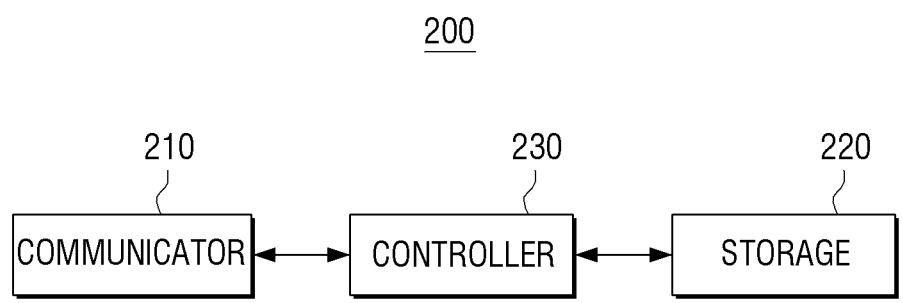
FIG. 10 is a block diagram illustrating a constitution of a server according to an exemplary embodiment.

FIG. 10 is a block diagram illustrating the server according to an exemplary embodiment. Referring to FIG. 10, the server 200 may include the communicator 210, the storage 220, and the controller 230.

The communicator 210 may perform communication with the UI providing apparatus 100. For example, the communicator 210 may perform communication with the UI providing apparatus 100 through the internet network, and transmit and receive various pieces of information. In this case, the communicator 210 may transmit and receive the information regarding the disability type and the degree of disability of a user, the UI output information, and the information regarding the modified UI with the UI providing apparatus 100.

The storage 220 may store various pieces of information. Specifically, the storage 220 may store the information regarding the disability type and the degree of disability matched per user. Thus, the storage 220 may store the information regarding the disability type and the degree of disability of a user per user identification information.

Further, the storage 220 may store the information regarding the UI output according to the disability type and the degree of disability of a user. Specifically, the storage 220 may include the UI type output from the UI providing apparatus 100, the size of the graphic UI and the output volume size of the voice UI according to the disability type and the degree of disability.

For example, when the degree of the vision impairment of a user is a level at which any object cannot be recognized by the user, the storage 220 may store the information indicating that the output UI type is the voice UI. Further, when the degree of the vision impairment of a user is a level at which an object of a preset size or more can be recognized by the user, the storage 220 may store the information indicating that the output UI type is the graphic UI or a combination of the graphic UI and the voice UI and the information regarding the size of the graphic UI.

Further, when the degree of hearing impairment of a user is a level at which any sound cannot be heard by the user, the storage 220 may store the information indicating that the output UI type is the graphic UI. Further, when the degree of hearing impairment of a user is a level at which a sound of a preset volume size or more can be heard by the user, the storage 220 may store the information indicating that the output UI type is the voice UI or a combination of the graphic UI and the voice UI and the information regarding the output volume size of the voice UI.

Further, the storage 220 may store the information regarding the modified UI. Thus, when the size of the graphic UI and the output volume size of the voice UI are modified in the UI providing apparatus 100 according to a user manipulation, the UI providing apparatus 100 may transmit the information regarding the modified UI to the server 200. Accordingly, the storage 220 may store the information regarding the modified UI received from the UI providing apparatus 100. In this case, the storage 220 may match and store the information regarding the modified UI per user information.

The controller 230 may control an operation of the server 200. Specifically, when the user identification information is received from the UI providing apparatus 100, the controller 230 may control so that the information regarding the disability type and the degree of disability corresponding to the user identification information is extracted and transmitted to the UI providing apparatus 100. Thus, as described above, when the user information received from the communication device 300 does not include the information regarding the disability type and the degree of disability of a user, the UI providing apparatus 100 may transmit the user identification information to the server 200. In this case, the controller 230 may extract the information regarding the disability type and the degree of disability of a user corresponding to the user identification information received from the UI providing apparatus 100 from the storage 220, and transmit to the UI providing apparatus 100 through the communicator 210.

Further, when the user information is received from the UI providing apparatus 100, the controller 230 may control the communicator 210 to transmit the UI output information corresponding to the disability type and the degree of disability to the UI providing apparatus 100.

Specifically, the controller 230 may control so that the UI output information corresponding to the user information is transmitted to the UI providing apparatus 100 by using the information stored in the storage 220, i.e., the information regarding the UI output according to the disability type and the degree of disability of a user. For example, when a user is determined to be a fourth level visually impaired user based on the user information received from the UI providing apparatus 100, the controller 230 may transmit the information indicating that the UI provided to the fourth level visually impaired user is the graphic UI and the information regarding the sizes of the UI components constituting the corresponding graphic UI based on the stored UI output information to the UI providing apparatus 100.

Further, when the information regarding the modified UI is received from the UI providing apparatus 100, the controller 230 may match and store the information regarding the modified UI per user. Next, when the user information is received, the controller 230 may control the communicator 210 to transmit the information regarding the modified UI to the UI providing apparatus 100.

As described above, when the information to output the UI corresponding to the disability type and the degree of disability of a user is not previously stored in the UI providing apparatus 100, the UI providing apparatus 100 may output the UI corresponding to the disability type and the degree of disability of a user by using the UI output information received from the server 200. Also, as described above, the UI providing apparatus 100 may transmit the information regarding the modified UI to the server 200 when the output state of the UI is modified by a user manipulation.

Accordingly, the controller 230 may match the information regarding the modified UI received from the UI providing apparatus 100 with the user information and store in the storage 220. Next, when the user information is received from the UI providing apparatus 100, the controller 230 may control the communicator 210 to transmit the information regarding the modified UI to the UI providing apparatus 100.

In this case, the controller 230 may normalize the information regarding the UI corresponding to the user information and the information regarding the modified UI, match and store the information regarding the normalized UI with the user information. For example, the controller 230 may normalize the size set for providing of the fourth level visually impaired user and the size adjusted by a user manipulation, and store the information regarding the size of the normalized graphic UI in the storage 160. In this case, the controller 230 may match and store the normalized size of the graphic UI with the corresponding user information. Thus, when the size set for the fourth level visual impairment is 7 and when the size adjusted by a user manipulation is 9, the normalized value of the above two values, i.e., 8, may be matched and stored with the fourth level visually impaired user.

FIGS. 11 to 15B are diagrams illustrating a method for providing the UI according to an exemplary embodiment.

Figure 11:
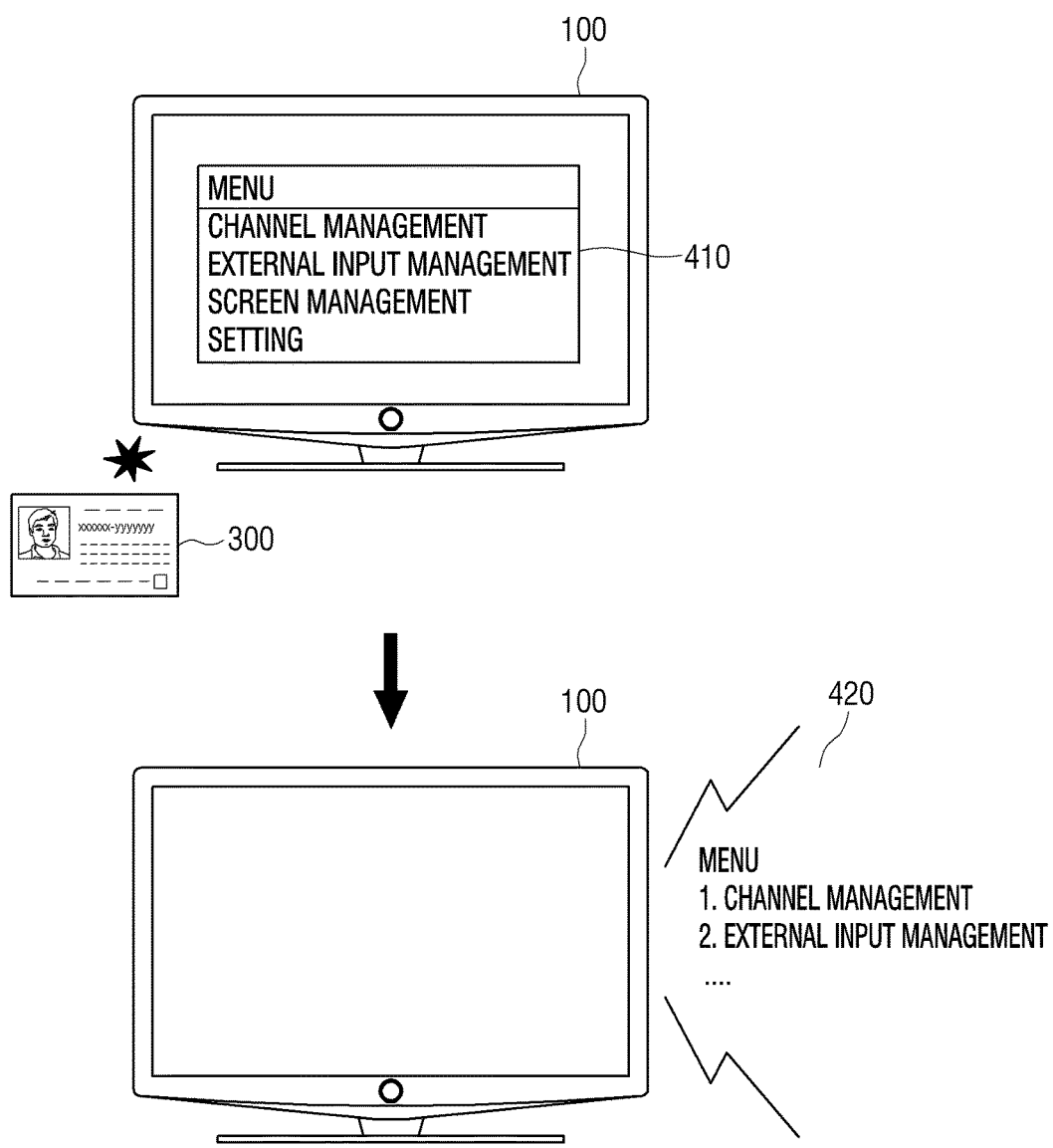
Figure 12:
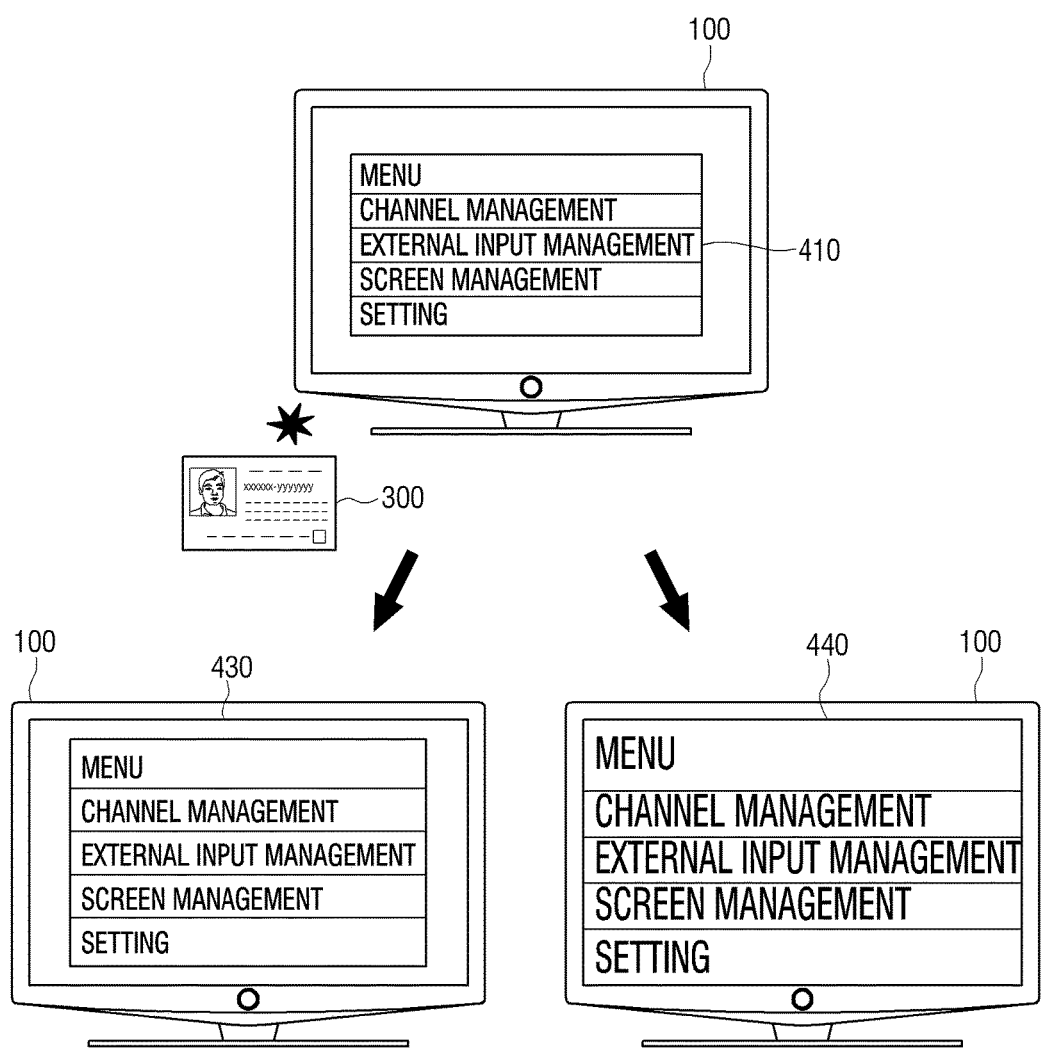

First, FIGS. 11 and 12 are diagrams illustrating a case in which a user is determined to be visually impaired according to the user information received from the communication device 300.

Accordingly, when a user is determined to be visually impaired, the UI providing apparatus 100 may output the voice UI. For example, as illustrated in FIG. 11, the UI providing apparatus 100 may not output an environment setting menu 410 with the graphic UI set by default, and output a voice UI 420 speaking the corresponding menu to receive a user command to select the corresponding menu.

Further, the UI providing apparatus 100 may output the graphic UI including the UI components having the size that can be recognized by a user according to the degree of the visual impairment. For example, as illustrated in FIG. 12, the UI providing apparatus 100 may display the environment setting menu 410 set by default in a bigger size. In this case, the UI providing apparatus 100 may adjust the size of the graphic UI according to degree of the vision impairment. Thus, the UI providing apparatus 100 may increase and output the size of an environment setting menu 440 provided for the relatively higher degree of vision impairment compared to an environment setting menu 430 provided for the relatively lower degree of vision impairment.

Figure 13:
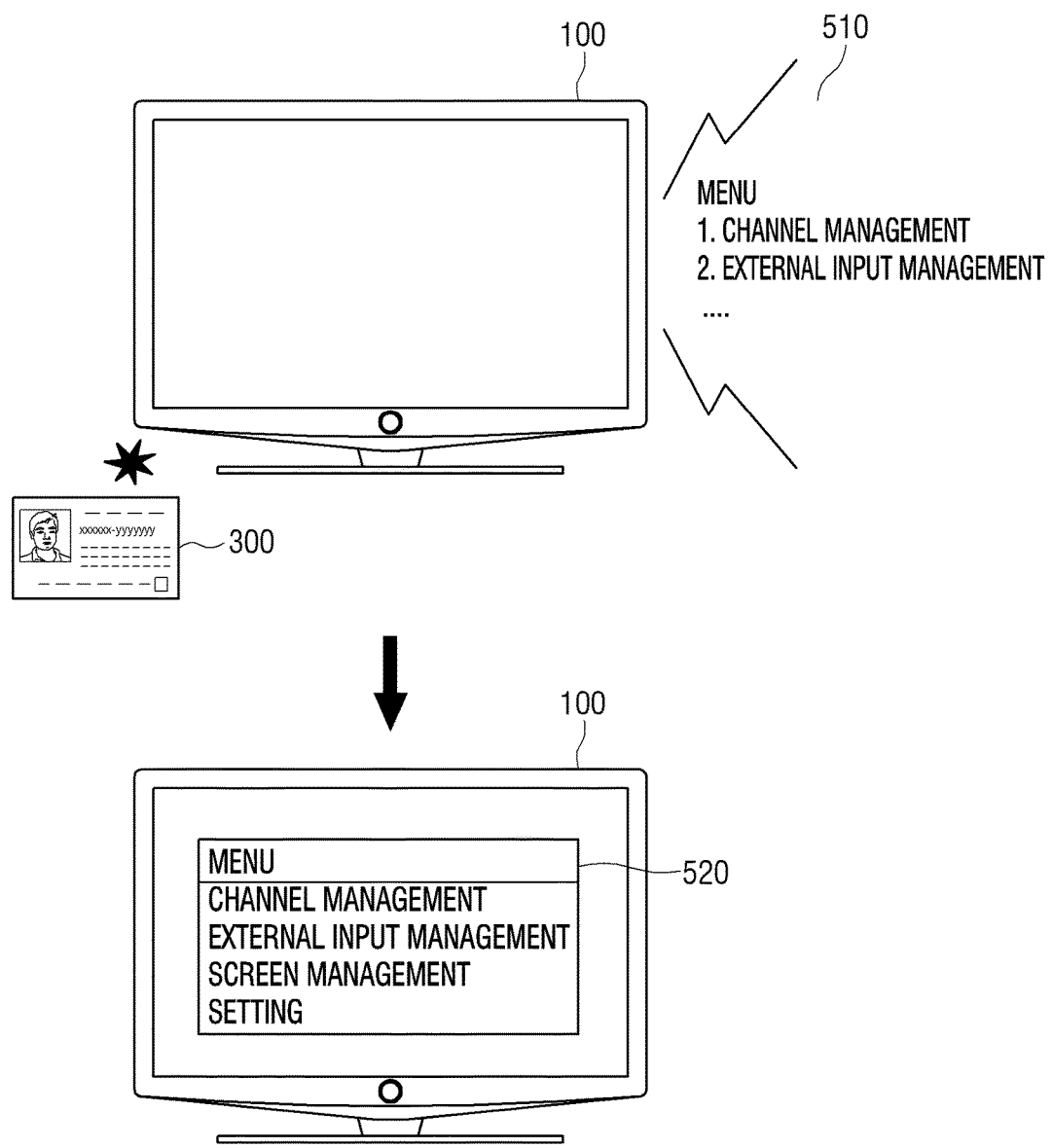

FIGS. 13 and 14 are diagrams illustrating a case in which a user is determined to be hearing-impaired according to the user information received from the communication device 300.

When a user is determined to be hearing-impaired, the UI providing apparatus 100 may output the graphic UI. For example, as illustrated in FIG. 13, the UI providing apparatus 100 may provide an environment setting menu 520 in the graphic form when a user is determined to be hearing-impaired even if the environment setting menu in a voice form 510 is set by default.

Further, the UI providing apparatus 100 may output the voice UI having the volume size that can be heard by a user according to the degree of hearing impairment. For example, as illustrated in FIG. 14, the UI providing apparatus 100 may output the voice UI set by default in a greater volume. In this case, the UI providing apparatus 100 may increase and output the output volume size of a voice UI 540 provided for the relatively higher degree of hearing impairment compared to a voice UI 530 provided for the relatively lower degree of hearing impairment.

Although the above exemplary embodiment describes that one of the graphic UI and the voice UI is output, this is merely an example. Thus, the UI providing apparatus 100 may output the graphic UI and the voice UI together according to the disability type and the degree of disability of a user. For example, the UI providing apparatus 100 may output the voice UI together with the graphic UI having the size that can be recognized by a user when a user is determined to be visually impaired. Further, when a user is determined to be hearing-impaired, the UI providing apparatus 100 may output the graphic UI together with the voice UI having the size that can be heard by a user.

Figure 15A:
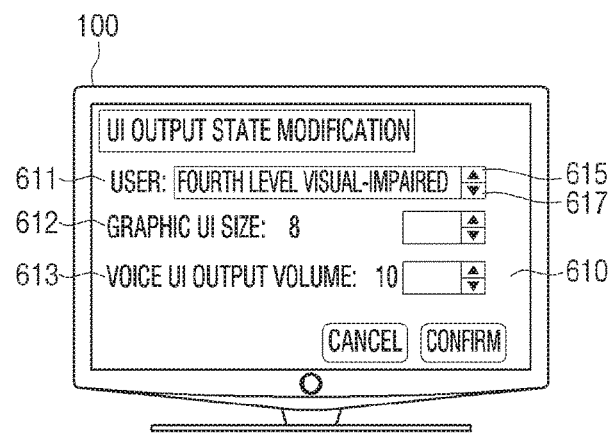
Figure 15B:
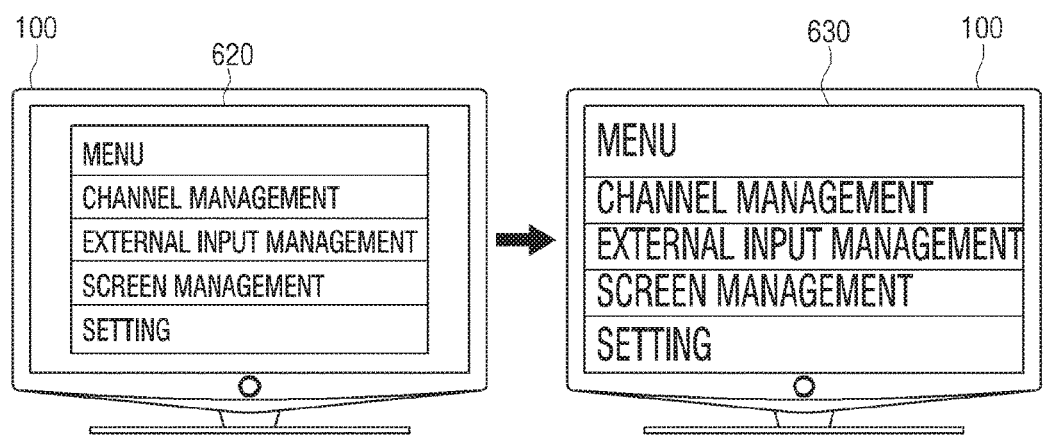

FIGS. 15A and 15B are diagrams illustrating a method for outputting the UI based on the information regarding the modified UI when the output state of the UI is modified.

First, as illustrated in FIG. 15A, the UI providing apparatus 100 may display a UI screen 610 to modify the output state of the UI based on a user manipulation. For example, the UI screen 610 may include a GUI 611 indicating the disability type and the degree of disability to be modified, a GUI 612 receiving a user manipulation to adjust the size of the graphic UI, and a GUI 613 receiving a user manipulation to adjust the output volume of the voice UI.

A user may modify the disability type and the degree of disability to be modified by selecting upper/lower buttons 615 and 617 provided on the GUI 611. For example, when the UI screen 610 displays the GUI 611 corresponding to the fourth level visually impaired user and a user selects the upper button 615 of the GUI 611, the UI screen may receive a user manipulation to modify the graphic UI and/or the voice UI to correspond to a fifth level visually impaired user. When a user selects the lower button 617 of the GUI 611, the UI screen may receive a user manipulation to modify the graphic UI and/or the voice UI to correspond to a third level visually impaired user. Further, a user may adjust the size of the graphic UI and the output volume size of the voice UI by selecting the upper/lower buttons provided on the GUI 612 and the GUI 613.

Accordingly, when a user modifies at least one among the size of the graphic UI and the output volume size of the voice UI on the UI screen 610, the UI providing apparatus 100 may store the information regarding the modified UI, and provide the UI corresponding to the disability type and the degree of disability of a user by using the information regarding the modified UI.

For example, FIG. 15B is a diagram illustrating the graphic UI output before and after the size of the graphic UI is modified by a user. As shown in an environment setting menu 620, UI components of the environment setting menu 620 have a size corresponding to the fourth level visually impaired user. However, after the size of the graphic UI is modified by a user, an environment setting menu 630 having the size modified by a user may be displayed for the fourth level visually impaired user.

Figure 16:
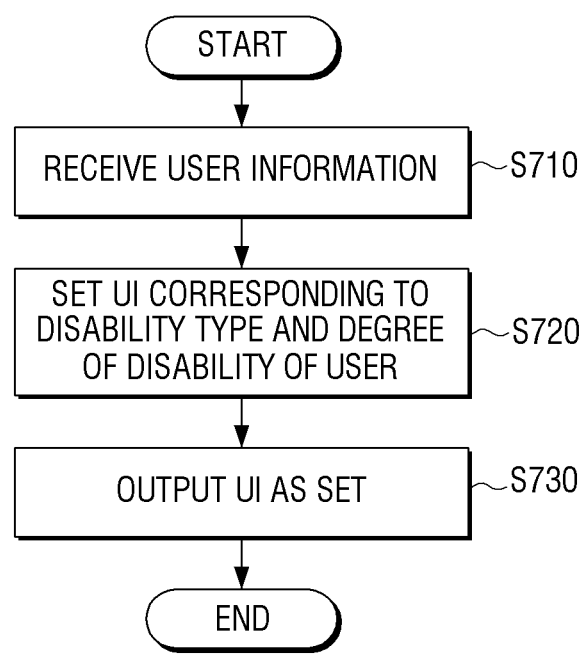
FIG. 16 is a flowchart illustrating a UI providing method of a UI providing apparatus according to an exemplary embodiment.

FIG. 16 is a flowchart illustrating a method for providing the UI of the UI providing apparatus according to an exemplary embodiment.

At S710, the user information may be received through the near field wireless communication with the communication device 300 storing the user information. In this case, the user information may be received through tagging with an NFC tag storing the user information by using an NFC reader. Herein, the user information may include at least one among the disability type, the degree of disability according to the disability type and the user identification information.

According to an exemplary embodiment, the user identification information may be transmitted to the server, and the information regarding the disability type and the degree of disability corresponding to the user identification information may be received from the server. Thus, when the user information received from the communication device 300 does not store the information regarding the disability type and the degree of disability of a user, the corresponding information may be received from the server.

At S720, the UI may be set correspondingly to the information regarding the disability type and the degree of disability of a user obtained based on the user information. At S730, the set UI may be output.

In an exemplary embodiment, when the disability type of a user is vision impairment, at least one among the graphic UI and the voice UI may be output according to the degree of the vision impairment. For example, when the degree of the vision impairment is higher than a preset level, the graphic UI having a preset size may be output. When the degree of the vision impairment is higher than a preset level, the voice UI may be output.

When the disability type of a user is hearing-impaired, at least one among the graphic UI and the voice UI may be output according to the degree of hearing impairment. More specifically, when the hearing-impaired level is lower than a preset level, the voice UI corresponding to a pertinent level may be output. Further, when the degree of hearing impairment is higher than a preset level, the graphic UI may be output.

According to an exemplary embodiment, when the UI providing apparatus does not store the information to output the UI corresponding to the disability type and the degree of disability, the user information may be transmitted to the server 200, and the UI output information corresponding to the disability type and the degree of disability may be received from the server 200. Accordingly, based on the information received from the server 200, the UI corresponding to the disability type and the degree of disability of a user may be output.

According to an exemplary embodiment, when receiving a user manipulation to modify the output state of the UI, modifying the output state of the UI according to a user manipulation, and receiving the user information, the modified UI may be output. Thus, when the sizes of the UI components included in the graphic UI are adjusted or when the output volume size of the voice UI is adjusted, the information regarding the modified UI may be stored. When the user information is received again, the UI corresponding to the disability type and the degree of disability of a user may be output by using the information regarding the modified UI.

In this case, when the output state of the UI is modified according to a user manipulation, the information regarding the modified UI may be transmitted to the server 200. As described above, when the information to output the UI corresponding to the disability type and the degree of disability of a user is not stored, the UI providing apparatus may receive the UI output information from the server 200, and output the UI corresponding to the disability type and the degree of disability of a user. Accordingly, when the UI corresponding to the disability type and the degree of disability of a user is output by using the UI output information received from the server 200, the UI providing apparatus may transmit the information regarding the modified UI to the server 200, and the server 200 may store the information regarding the modified UI.

The operations or steps of the methods or algorithms described above can be embodied as computer readable codes on a computer readable recording medium, or to be transmitted through a transmission medium. The computer readable recording medium is any data storage device that can store data which can be thereafter read by a computer system. Examples of the computer readable recording medium include a read-only memory (ROM), a random-access memory (RAM), a compact disc (CD)-ROM, a digital versatile disc (DVD), a magnetic tape, a floppy disk, and an optical data storage device, not being limited thereto. The transmission medium can include carrier waves transmitted through the Internet or various types of communication channel. The computer readable recording medium can also be distributed over network coupled computer systems so that the computer readable code is stored and executed in a distributed fashion.

At least one of the components, elements or units represented by a block as illustrated in FIGS. 1 and 7-10 may be embodied as various numbers of hardware, software and/or firmware structures that execute respective functions described above, according to an exemplary embodiment. For example, at least one of these components, elements or units may use a direct circuit structure, such as a memory, processing, logic, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in the above block diagrams, communication between the components, elements or units may be performed through the bus. Functional aspects of the above exemplary embodiments may be implemented in algorithms that execute on one or more processors. Furthermore, the components, elements or units represented by a block or processing steps may employ any number of related art techniques for electronics configuration, signal processing and/or control, data processing and the like.

With the UI providing apparatus and the UI providing method according to various exemplary embodiments explained above, user convenience can be enhanced because a user can be provided with different UIs according to the disability type and the degree of disability.

The foregoing embodiments and advantages are merely exemplary and are not to be construed as limiting. The present teaching can be readily applied to other types of apparatuses. Also, the description of the embodiments is intended to be illustrative, and not to limit the scope of the claims, and many alternatives, modifications, and variations will be apparent to those skilled in the art.

The invention claimed is:

1. An electronic apparatus, comprising:
    a receiver circuitry; and
    a processor configured to:
        receive user information through the receiver circuitry with an external device, the external device being configured to store the user information;
        identify whether a user is disabled based on the received user information,
        based on identifying that the user is disabled, obtain disability information including a disability type of the user and a degree of disability of the user,
        identify at least one UI from among a first UI comprising a graphic UI, a second UI comprising a voice UI, and a third UI comprising the graphic UI and the voice UI based on the disability information, and
        provide the identified at least one UI,
    wherein the receiver circuitry comprises a near field communication (NFC) reader configured to receive the user information through tagging with an NFC tag, the NFC tag being configured to store the user information,
    wherein the processor is configured to output the graphic UI or the voice UI based on the degree of disability being lower than a first preset level, and output the voice UI and the graphic UI based on the degree of disability being higher than the first preset level.

2. The electronic apparatus as claimed in claim 1, wherein the user information comprises at least one from among information about the disability type, information about the degree of disability according to the disability type, and user identification information.

3. The electronic apparatus as claimed in claim 2, further comprising:
    a communicator configured to perform communication with a server,
    wherein the processor is configured to control the communicator to transmit the user identification information to the server, and receive the disability information corresponding to the user identification information, from the server.

4. The electronic apparatus as claimed in claim 2, wherein the processor configured to, according to a degree of vision impairment in response to the disability type of the user being the vision impairment, perform at least one of:
    providing a video corresponding to the graphic UI;
    providing a sound corresponding to the voice UI; or
    providing a combination of the graphic UI and the voice UI.

5. The electronic apparatus as claimed in claim 4, wherein the processor is configured to control to provide the graphic UI in response to the degree of the vision impairment being lower than a second preset level, and provide the voice UI in response to the degree of the vision impairment being higher than the second preset level.

6. The electronic apparatus as claimed in claim 2, wherein the processor is further configured to, according to a degree of hearing impairment in response to the disability type of the user being the hearing impairment, perform at least one of:
    providing a video corresponding to the graphic UI;
    providing a sound corresponding to the voice UI; or
    providing a combination of the graphic UI and the voice UI.

7. The electronic apparatus as claimed in claim 6, wherein the processor is configured to control to provide the voice UI in response to the degree of the hearing impairment being lower than a third preset level and provide the graphic UI in response to the degree of the hearing impairment being higher than the third preset level.

8. The electronic apparatus as claimed in claim 1, further comprising:
a communicator configured to perform communication with a server, wherein the processor is further configured to control the communicator to transmit the user information to the server when the disability information is not stored in the UI providing apparatus, and receive the disability information from the server.

9. The electronic apparatus as claimed in claim 1, further comprising:
an inputter circuitry configured to receive a user input for modifying an output state of the UI, wherein the processor is further configured to control to provide a modified UI in response to the user information being received.

10. The electronic apparatus as claimed in claim 9, further comprising:
a communicator configured to perform communication with a server, wherein the processor is further configured to control the communicator to transmit information regarding the modified UI to the server in response to the output state of the UI being modified according to the user input.

11. A controlling method of an electronic device comprising a processor, the method comprising:
receiving, by the processor, user information through communication with an external device, the external device being configured to store the user information;
identifying, by the processor, whether a user is disabled based on the received user information;
based on identifying that the user is disabled, obtaining, by the processor, disability information including a disability type of the user and a degree of disability of the user;
identifying, by the processor, at least one UI from among a first UI comprising a graphic UI, a second UI comprising a voice UI and a third UI comprising the graphic UI and the voice UI based on the disability information; and
providing, by the processor, the identified at least one UI,
wherein the receiving comprises receiving the user information through tagging with a near field communication (NFC) tag by using an NFC reader, the NFC tag being configured to store the user information, and
wherein the providing comprises outputting the graphic UI or the voice UI based on the degree of disability being lower than a preset level, and outputting the voice UI and the graphic UI based on the degree of disability being higher than the preset level.

12. The method as claimed in claim 11, wherein the user information comprises at least one from among information about the disability type, information about the degree of disability and user identification information.

13. The method as claimed in claim 12, further comprising:
transmitting the user identification information to a server; and
receiving the disability information, based on the user identification information, from the server.

14. An apparatus for providing a user interface (UI), the apparatus comprising:
at least one memory operable to store program code; and
at least one processor operable to read the program code and operate as instructed by the program code,
wherein the program code causes the at least one processor to:
receive user information and identify whether a user is disabled based on the received user information,
based on identifying that the user is disabled, obtain disability information including a disability type of the user and a degree of disability of the user,
identify at least one UI from among a first UI comprising a graphic UI, a second UI comprising a voice UI and a third UI comprising the graphic UI and the voice UI based on the disability information, and
provide the identified at least one UI,
wherein the program code further causes the at least one processor to:
receive the user information through tagging with a near field communication (NFC) tag by using an NFC reader, the NFC tag being configured to store the user information, and
output the graphic UI or the voice UI based on the degree of disability being lower than a preset level, and output the voice UI and the graphic UI based on the degree of disability being higher than the preset level.

15. The apparatus of claim 14, wherein the user information is received through communication with an external device, the external device being configured to store the user information.

16. The apparatus of claim 15, further comprising a near field communication (NFC) reader configured to receive the user information through tagging with an NFC tag, the NFC tag being configured to store the user information.

17. The apparatus of claim 14, wherein the user information comprises at least one from among information about the disability type and information about the degree of disability.

18. The apparatus of claim 17, wherein the program code causes the at least one processor to receive user identification and obtain the user information based on the user identification.

* * * * *